US009082277B2

(12) United States Patent
Howard et al.

(10) Patent No.: US 9,082,277 B2
(45) Date of Patent: *Jul. 14, 2015

(54) METHOD, SYSTEM AND WIRELESS DEVICE FOR MONITORING PROTECTIVE HEADGEAR

(75) Inventors: John W. Howard, Cedar Park, TX (US); Richard Cutler, Leander, TX (US)

(73) Assignee: THL Holding Company, LLC, Round Rock, TX (US)

( * ) Notice: Subject to any disclaimer, the term of this patent is extended or adjusted under 35 U.S.C. 154(b) by 508 days.

This patent is subject to a terminal disclaimer.

(21) Appl. No.: 13/309,728

(22) Filed: Dec. 2, 2011

(65) Prior Publication Data

US 2012/0077439 A1 Mar. 29, 2012

Related U.S. Application Data

(63) Continuation-in-part of application No. 12/713,316, filed on Feb. 26, 2010, now Pat. No. 8,253,559.

(60) Provisional application No. 61/558,764, filed on Nov. 11, 2011.

(51) Int. Cl.

| | |
|---|---|
| ***G08B 1/00*** | (2006.01) |
| ***G08B 23/00*** | (2006.01) |
| ***A61B 5/103*** | (2006.01) |
| ***G01C 9/00*** | (2006.01) |
| ***H03F 1/26*** | (2006.01) |
| ***G08B 13/14*** | (2006.01) |
| ***G08B 21/02*** | (2006.01) |
| ***G08B 25/01*** | (2006.01) |

(52) U.S. Cl.

CPC ........ *G08B 13/1427* (2013.01); *G08B 21/0244* (2013.01); *G08B 21/0247* (2013.01); *G08B 21/0269* (2013.01); *G08B 21/0272* (2013.01); *G08B 21/0277* (2013.01); *G08B 25/016* (2013.01)

(58) Field of Classification Search

None

See application file for complete search history.

(56) References Cited

U.S. PATENT DOCUMENTS

| | | | | |
|---|---|---|---|---|
| 5,539,935 | A | 7/1996 | Rush | |
| 6,589,189 | B2 | 7/2003 | Meyerson | |
| 6,826,509 | B2 * | 11/2004 | Crisco et al. | 702/141 |
| 6,941,952 | B1 | 9/2005 | Rush | |
| 7,526,389 | B2 * | 4/2009 | Greenwald et al. | 702/55 |
| 7,570,170 | B2 | 8/2009 | Wallner | |
| 8,466,794 | B2 * | 6/2013 | Mack et al. | 340/573.1 |
| 8,537,017 | B2 * | 9/2013 | Mack et al. | 340/573.1 |
| 2002/0060633 | A1 * | 5/2002 | Crisco et al. | 340/669 |
| 2006/0139166 | A1 * | 6/2006 | Choutier et al. | 340/539.12 |
| 2006/0189852 | A1 | 8/2006 | Greenwald | |
| 2011/0181418 | A1 * | 7/2011 | Mack et al. | 340/573.1 |
| 2011/0181420 | A1 * | 7/2011 | Mack et al. | 340/573.1 |
| 2011/0184320 | A1 * | 7/2011 | Shipps et al. | 600/595 |
| 2011/0184663 | A1 * | 7/2011 | Mack et al. | 702/41 |
| 2012/0075095 | A1 * | 3/2012 | Howard et al. | 340/539.12 |
| 2012/0077440 | A1 * | 3/2012 | Howard et al. | 455/41.2 |

(Continued)

*Primary Examiner* — Julie Lieu

(74) *Attorney, Agent, or Firm* — Garlick & Markison; Bruce E. Stuckman

(57) ABSTRACT

A wireless device includes a sensor module that generates sensor data in response to an impact to the protective headgear. The sensor module includes an accelerometer and a gyroscope and wherein the sensor data includes linear acceleration data and rotational velocity data. A device processing module generates event data in response to the sensor data. A short-range wireless transmitter transmits a wireless signal that includes the event data.

17 Claims, 15 Drawing Sheets

(56) References Cited

U.S. PATENT DOCUMENTS

2012/0077441 A1* 3/2012 Howard et al. .............. 455/41.2
2012/0191397 A1* 7/2012 Eatwell ........................... 702/94
2012/0210498 A1* 8/2012 Mack ................................ 2/414
2012/0223833 A1* 9/2012 Thomas et al. .......... 340/539.12
2012/0304365 A1* 12/2012 Howard et al. ................... 2/410
2012/0304367 A1* 12/2012 Howard et al. ................... 2/413
2012/0304767 A1* 12/2012 Howard et al. ............ 73/504.03
2012/0306438 A1* 12/2012 Howard et al. ............... 320/107
2012/0306639 A1* 12/2012 Howard et al. ............ 340/539.1
2012/0306641 A1* 12/2012 Howard et al. .......... 340/539.11
2012/0306642 A1* 12/2012 Howard et al. .......... 340/539.11
2012/0309300 A1* 12/2012 Howard et al. ................. 455/39
2013/0060168 A1* 3/2013 Chu et al. ...................... 600/595
2013/0110415 A1* 5/2013 Davis et al. ..................... 702/41
2013/0271602 A1* 10/2013 Bentley et al. ................ 348/143
2013/0282308 A1* 10/2013 Mack et al. ..................... 702/41
2014/0039355 A1* 2/2014 Crisco et al. .................. 600/595

* cited by examiner

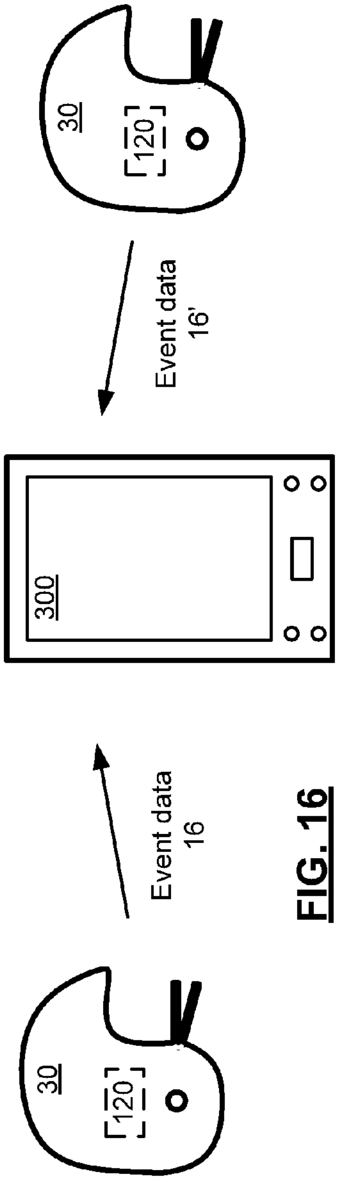
FIG. 16
FIG. 17
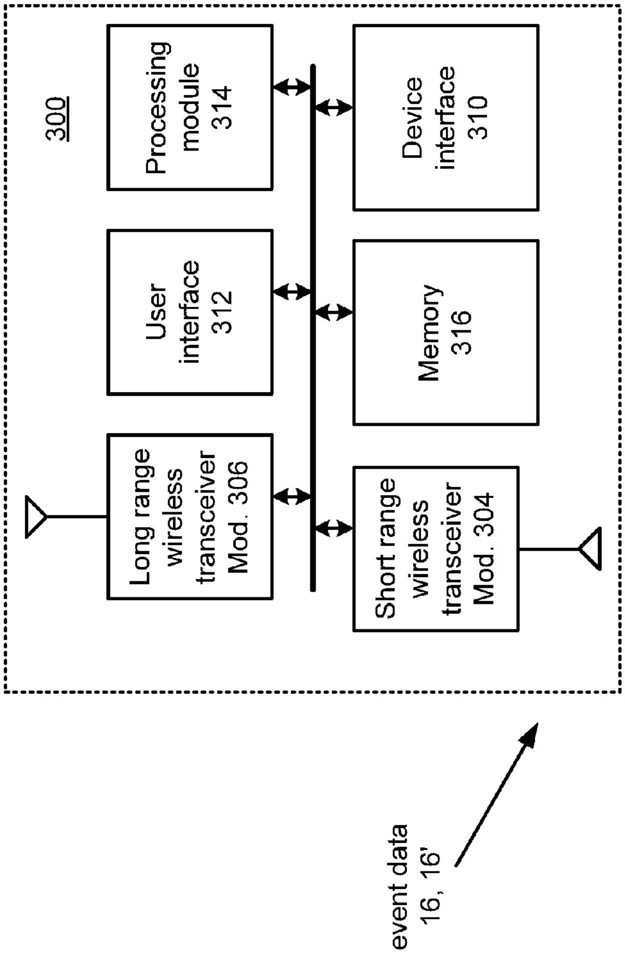

METHOD, SYSTEM AND WIRELESS DEVICE FOR MONITORING PROTECTIVE HEADGEAR

CROSS REFERENCE TO RELATED APPLICATIONS

The present application claims priority under 35 USC 119 to the provisionally filed application, METHOD, SYSTEM AND WIRELESS DEVICE FOR MONITORING PROTECTIVE HEADGEAR, having Ser. No. 61/558,764, filed on Nov. 11, 2011; the contents of which is expressly incorporated herein in its entirety by reference thereto.

The present application also claims priority under 35 USC 120 as a continuation in part to the U.S. publication number 2011/0210847, entitled "SYSTEM AND WIRELESS DEVICE FOR LOCATING A REMOTE OBJECT", having Ser. No. 12/713,316 filed on Feb. 26, 2010; the contents of which is expressly incorporated herein in its entirety by reference thereto.

BACKGROUND OF THE INVENTION

1. Technical Field of the Invention

The present invention relates to wireless communication devices and further to protective headgear.

2. Description of Related Art

As is known, wireless communication devices are commonly used to access long range communication networks as well as broadband data networks that provide text messaging, email services, Internet access and enhanced features such as streaming audio and video, television service, etc., in accordance with international wireless communications standards such as 2G, 2.5G, 3G and 4G. Examples of such networks include wireless telephone networks that operate cellular, personal communications service (PCS), general packet radio service (GPRS), global system for mobile communications (GSM), and integrated digital enhanced network (iDEN).

Many wireless telephones have operating systems that can run applications that perform additional features and functions. Apart from strictly wireless telephony and messaging, wireless telephones have become general platforms for a plethora of functions associated with, for example, navigational systems, social networking, electronic organizers, audio/video players, shopping tools, and electronic games. Users have the ability to choose a wireless telephone and associated applications that meet the particular needs of that user.

U.S. Pat. Nos. 5,539,935, 6,589,189, 6,826,509, 6,941,952, 7,570,170 and published US Patent Application number 2006/0189852 describe systems that attach accelerometers to a protective helmet, either on the exterior of the helmet itself, or on the surface of the pads forcing sensors into direct contact with the wearer's head. Some use a single sensor (1, 2 or 3 axis), while others use sensors positioned at various locations on the head or helmet. An example is U.S. Pat. No. 6,826,509 that describes a specific orientation of the accelerometer's axis with respect to the skull of the wearer and describes a method that estimates the point of impact contact, the direction of force applied, and the duration of an impact in terms of its acceleration. The method of calculating these parameters applies an error-minimizing scheme that "best fits" the array of accelerometer inputs. The common goal of all such systems is to determine if an impact event has exceeded a threshold that would warrant examining the individual involved for signs of a concussion and possible removal from the activity. Some systems combine the impact threshold information with some form of follow-up physiological evaluation such as memory, eye sight, balance, or awareness tests. These tests purportedly determine if a concussion has occurred and provide some insight into its severity. Another goal of some systems is to provide information about the impact event that may be helpful in diagnosis and treatment, such as a display of the point of impact, direction, and duration of an acceleration overlaid on a picture of a head.

The disadvantages of conventional approaches will be evident to one skilled in the art when presented the disclosure that follows.

BRIEF SUMMARY OF THE INVENTION

The present invention is directed to various system, apparatus and methods of operation that are further described in the following Brief Description of the Drawings, the Detailed Description of the Invention, and the claims. Other features and advantages of the present invention will become apparent from the following detailed description of the invention made with reference to the accompanying drawings.

BRIEF DESCRIPTION OF THE SEVERAL VIEWS OF THE DRAWINGS

FIG. 16 presents a pictorial representation of a system for monitoring protective headgear in accordance with an embodiment of the present invention.

FIG. 17 presents a schematic block diagram of a handheld wireless device 300 in accordance with an embodiment of the present invention.

DETAILED DESCRIPTION OF THE INVENTION

Figure 1:
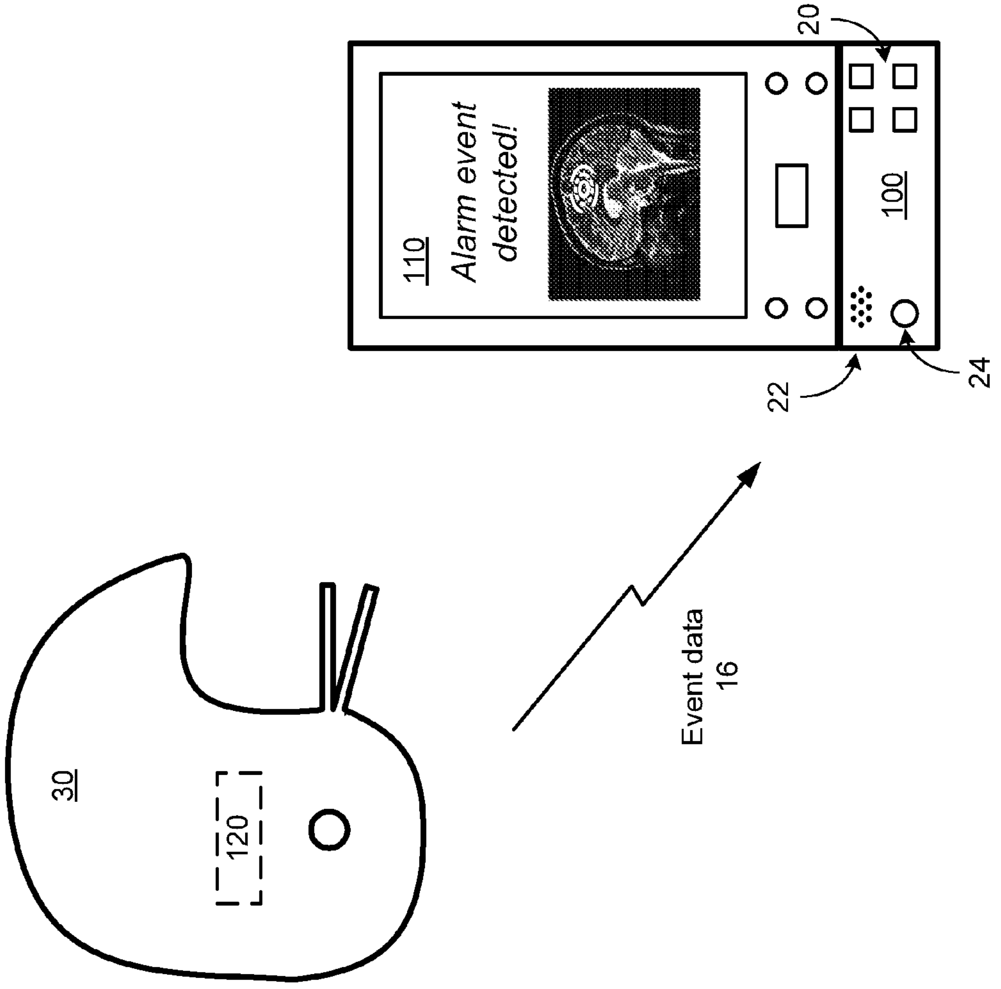
FIG. 1 presents a pictorial representation of a system for monitoring protective headgear in accordance with an embodiment of the present invention.

FIG. 1 presents a pictorial representation of a system for monitoring protective headgear in accordance with an embodiment of the present invention. In particular, a handheld communication device 110, such as a smart phone, digital book, netbook, personal computer with wireless data communication or other wireless communication device includes a wireless transceiver for communicating over a long range wireless network such as a cellular, PCS, CDMA, GPRS, GSM, iDEN or other wireless communications network and/or a short-range wireless network such as an IEEE 802.11 compatible network, a Wimax network, another wireless local area network connection or other communications link. Handheld communication device 110 is capable of engaging in wireless communications such as sending and receiving telephone calls and/or wireless data in conjunction with text messages such as emails, short message service (SMS) messages, pages and other data messages that may include multimedia attachments, documents, audio files, video files, images and other graphics. Handheld communication device 110 includes one or more processing devices for executing other applications and a user interface that includes, for example, buttons, a display screen such as a touch screen, a speaker, a microphone, a camera for capturing still and/or video images and/or other user interface devices.

A wireless device 120 is mounted in or otherwise coupled to a piece of protective headgear 30. The wireless device 120 includes a sensor module that generates sensor data in response to an impact to the protective headgear 30. Wireless device 120 further includes a short-range wireless transmitter that transmits a wireless signal, such as a radio frequency (RF) signal, magnetic signal, infrared (IR) signal or other wireless signal that includes data, such as event data 16 or other data that indicates, for example, data pertaining to an impact on the protective headgear. The short-range wireless transmitter can be part of a transceiver that operates in conjunction with a communication standard such as 802.11, Bluetooth, ZigBee, ultra-wideband, an RF identification (RFID), IR Data Association (IrDA), Wimax or other standard short or medium range communication protocol, or other protocol.

While protective headgear 30 is styled as a football helmet, the present invention can be implemented in conjunction with other protective headgear including a hat, headband, mouth guard or other headgear used in sports, other headgear and helmets worn by public safety or military personnel or other headgear or helmets.

Adjunct device 100 includes a housing that is coupleable to the handheld communication device 110 via a communication port of the handheld communication device 110. The adjunct device 100 includes a short-range wireless receiver that receives a wireless signal from the wireless device 120 that includes data, such as event data 16. The short-range wireless receiver of adjunct 100 can also be part of a transceiver that operates in conjunction with a communication standard such as 802.11, Bluetooth, ZigBee, ultra-wideband, Wimax or other standard short or medium range communication protocol, or other protocol. In particular, the short-range wireless receiver of adjunct device 100 is configured to receive the event data 16 or other data generated by wireless device 120.

Adjunct device includes its own user interface having push buttons 20, sound emitter 22 and light emitter 24 that optionally can emit audio and/or visual alert signals in response to the event data 16. As with the user interface of wireless device 120, the user interface of adjunct device 100 can similarly include other devices such as a touch screen or other display screen, a thumb wheel, trackball, and/or other input or output devices. While shown as a plug-in module, the adjunct device 100 can be implemented as either a wireless gateway or bridge device or a case or other housing that encloses or partially encloses the handheld communication device 100.

In operation, event data 16 is generated by wireless device 120 in response to an impact to the protective headgear 30. The event data 16 is transmitted to the adjunct device 100 that transfers the event data 16 to the handheld communication device 110 either wirelessly or via the communication port of the handheld communication device 110. The handheld communication device 110 executes an application to further process the event data 16 to, for example, display a simulation of the head and/or brain of the wearer of the protective headgear 30 as a result of the impact.

The further operation of wireless device 120, adjunct device 100 and handheld communication device 100, including several optional implementations, different features and functions spanning complementary embodiments are presented in conjunction with FIGS. 2-24 that follow.

Figure 3:
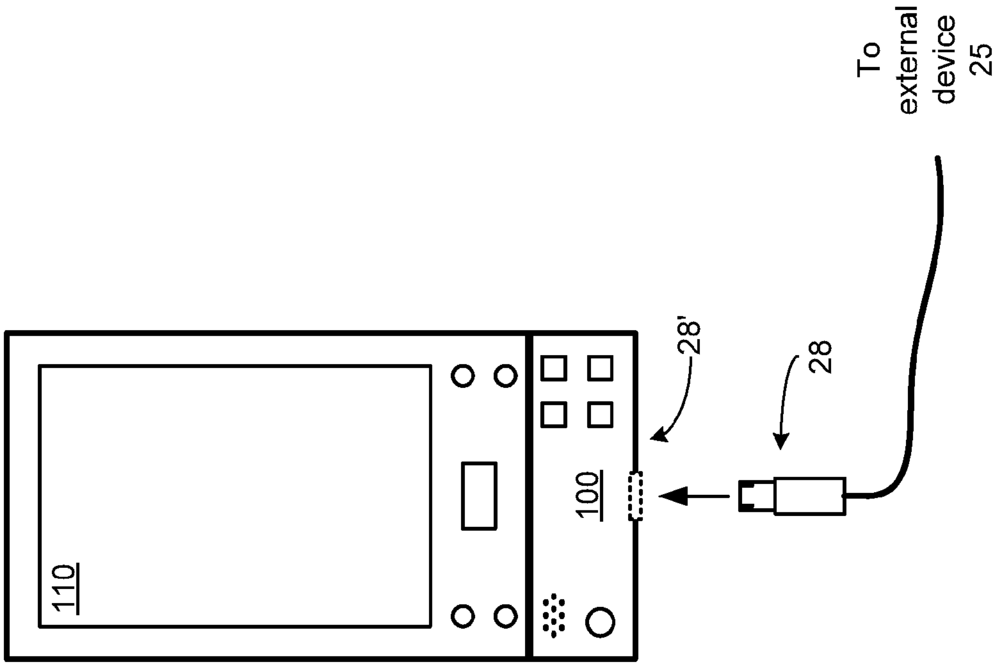
FIG. 3 presents a pictorial representation of handheld communication device 110 and adjunct device 100 in accordance with an embodiment of the present invention.
Figure 2:
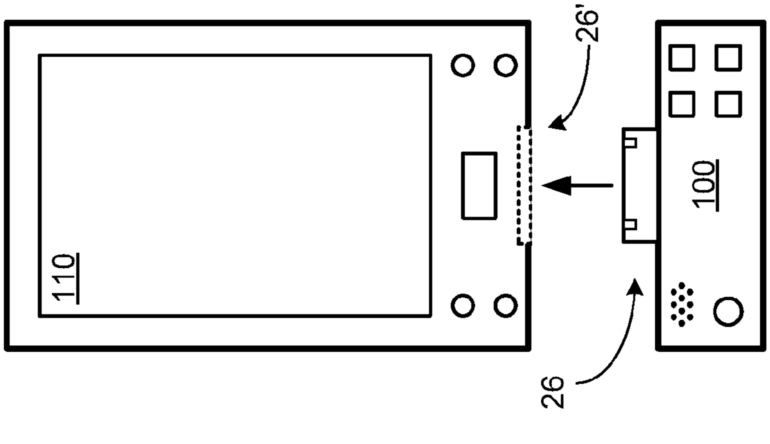
FIG. 2 presents a pictorial representation of handheld communication device 110 and adjunct device 100 in accordance with an embodiment of the present invention.

FIGS. 2 and 3 present pictorial representations of handheld communication device 110 and adjunct device 100 in accordance with an embodiment of the present invention. As shown in FIG. 2, adjunct device 100 and handheld communication device 110 are decoupled. Handheld communication device 110 includes a communication port 26' and adjunct device 100 includes a mating plug 26 for coupling the adjunct device 100 to the communication port 26' of handheld communication device 110. In an embodiment of the present invention, the communication port 26' and plug 26 are configured in conjunction with a standard interface such as universal serial bus (USB), Firewire, or other standard interface, however, a device specific communication port such as an Apple iPod/iPhone port, a Motorola communication port or other communication port can likewise be employed. Further, while a physical connection is shown, a wireless connection, such as a Bluetooth link, 802.11 compatible link, an RFID connection, IrDA connection or other wireless connection can be employed in accordance with alternative embodiments.

As shown in FIG. 3, adjunct device 100 is coupled to the handheld communication device 110 by plug 26 being inserted in communication port 26'. Further, adjunct device 100 includes its own communication port 28' for coupling, via a mating plug 28, the adjunct device 100 to an external device 25, such as a computer or other host device, external charger or peripheral device. In an embodiment of the present invention, the communication port 28' and plug 28 are configured in conjunction with a standard interface such as universal serial bus (USB), Firewire, or other standard interface, however, a device specific communication port such as an Apple iPod/iPhone port, a Motorola communication port or other communication port can likewise be employed.

In an embodiment of the present invention, the adjunct device passes signaling between the external device 25 and the handheld communication device 110 including, for instance, charging signals from the external connection and data communicated between the handheld communication device 110 and the external device 25. In this fashion, the external device can communicate with and/or charge the handheld communication device with the adjunct device 100 attached, via pass through of signals from plug 28 to communication port 26'. It should be noted however, that while communication ports 28' and 26' can share a common physical configuration, in another embodiment of the present invention, the communication ports 28' and 26' can be implemented via different physical configurations. For example, communication port 26' can be implemented via a device specific port that carries USB formatted data and charging signals and communication port 28' can be implemented via a standard USB port. Other examples are likewise possible.

In an embodiment of the present invention, when the adjunct device 100 is coupled to handheld communication device 110, the adjunct device 100 initiates communication via the communication port 26' to determine if an application is loaded in the handheld communication device 110—to support the interaction with the adjunct device 100. Examples of such applications include a headgear monitoring application or other application that operates in conjunction with the adjunct 100. If no such application is detected, the adjunct 100 can communicate via communication port 26' to initiate a download of such an application directly or to send the browser of the handheld communication device 110 to a website store at a remote server or other location where supporting applications can be browsed, purchased or otherwise selected for download to the handheld communication device 110.

In a further embodiment of the present invention, when a supporting application is loaded in handheld communication device 110, the handheld communication device 110 initiates communications via the communication port 26' to determine if an adjunct device 100 is coupled thereto or whether or not an adjunct device has never been coupled thereto. If no such adjunct device 100 is detected, the application can instruct the user to connect the adjunct device 100. Further, the application can, in response to user selection and/or an indication that an adjunct device has not been previously coupled to the handheld communication device 110, automatically direct a browser of the handheld communication device 110 to a website store at a remote server or other location where a supporting adjunct devices 100 can be selected and purchased, in order to facilitate the purchase of an adjunct device, via the handheld communication device 110.

In a further embodiment, the application maintains a flag that indicates if an adjunct device 100 has previously been connected. In response to an indication that an adjunct device has not been previously coupled to the handheld communication device 110, the application can automatically direct a browser of the handheld communication device 110 to a website store at a remote server or other location where a supporting adjunct devices 100 can be selected and purchased, in order to facilitate the purchase of an adjunct device, via the handheld communication device 110.

Figure 4:
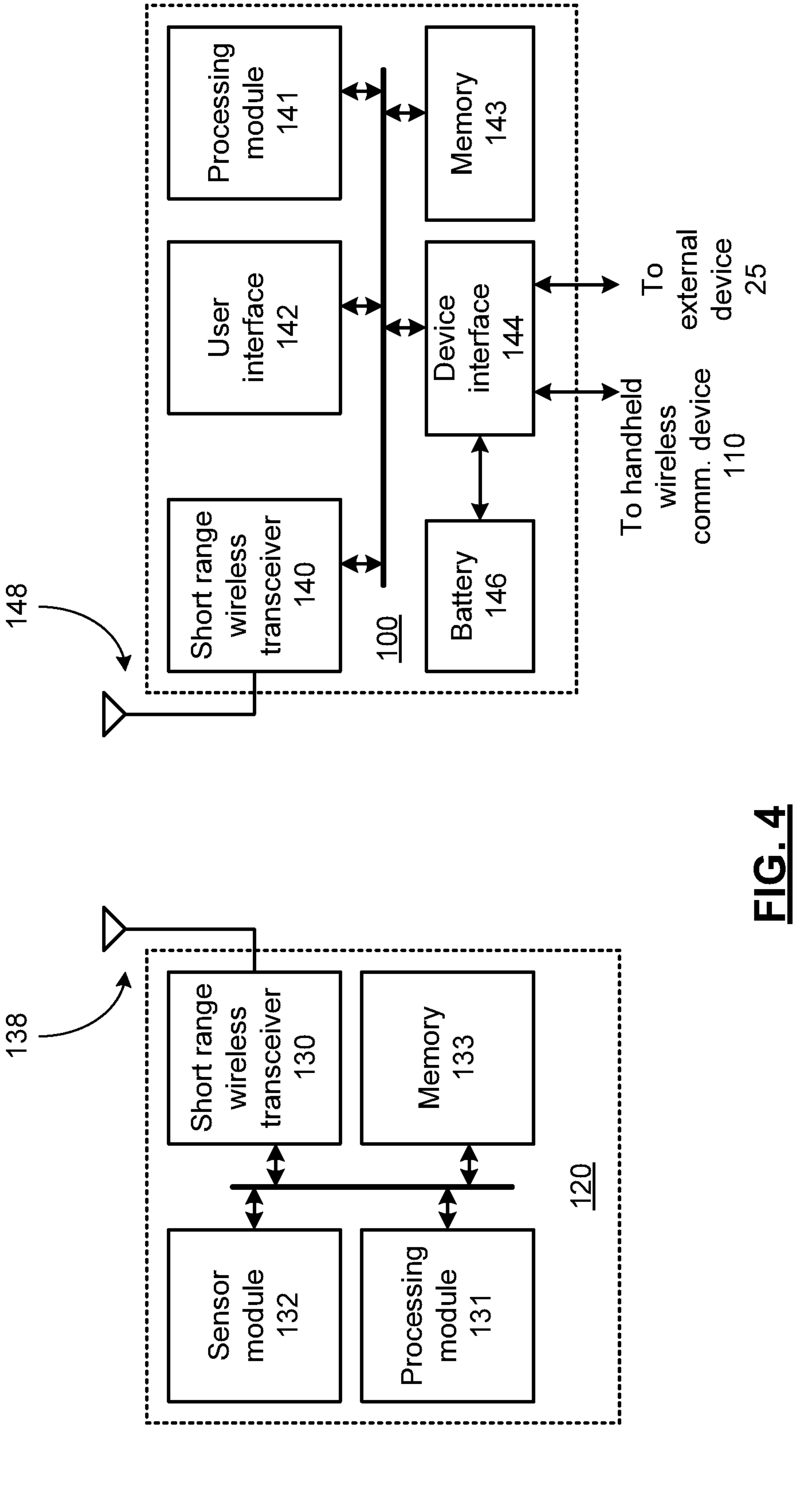
FIG. 4 presents a schematic block diagram of a wireless device 120 and adjunct device 100 in accordance with an embodiment of the present invention.

FIG. 4 presents a schematic block diagram of a wireless device 120 and adjunct device 100 in accordance with an embodiment of the present invention. In particular, wireless device 120 includes short-range wireless transceiver 130 coupled to antenna 138, processing module 131, sensor module 132 and memory 133. While not expressly shown, wireless device 120 can include a replaceable battery for powering the components of wireless device 120. In the alternative, wireless device 120 can include a battery that is rechargeable via an external charging port, for powering the components of wireless device 120. In addition, the wireless device 120 can be powered in whole or in part via any electromagnetic or kinetic energy harvesting system, such as an electromagnetic carrier signal in a similar fashion to a passive RF tag or passive RFID device, via a piezoelectric element that generates a voltage and current in response to an impact event and/or via capacitive storage of a charge sufficient to power the wireless device 120 for short intervals of time, such as during an event window. Adjunct device 100 includes short-range wireless transceiver 140 coupled to antenna 148, processing module 141, user interface 142 and memory 143, device interface 144, and battery 146. The processing modules 131 and 141 control the operation of the wireless device 120 and adjunct device 100, respectively and provide further functionality described in conjunction with, and as a supplement to, the functions provided by the other components of wireless device 120 and adjunct device 100.

As discussed in conjunction with FIGS. 1-4, the short-range wireless transceivers 130 and 140 each can be implemented via a transceiver that operates in conjunction with a communication standard such as 802.11, Bluetooth, ZigBee, ultra-wideband, RFID, IrDA, Wimax or other standard short or medium range communication protocol, or other protocol. User interface 142 can contain one or more push buttons, a sound emitter, light emitter, a touch screen or other display screen, a thumb wheel, trackball, and/or other user interface devices.

The processing module 131 can be implemented using a microprocessor, micro-controller, digital signal processor, microcomputer, central processing unit, field programmable gate array, programmable logic device, state machine, logic circuitry, analog circuitry, digital circuitry, and/or any device that manipulates signals (analog and/or digital) based on operational instructions that are stored in memory, such as memory 133. Note that when the processing module 131 implements one or more of its functions via a state machine, analog circuitry, digital circuitry, and/or logic circuitry, the memory storing the corresponding operational instructions may be embedded within, or external to, the circuitry comprising the state machine, analog circuitry, digital circuitry, and/or logic circuitry. Further note that, the memory module 133 stores, and the processing module 131 executes, operational instructions corresponding to at least some of the steps and/or functions illustrated herein.

The memory module 133 may be a single memory device or a plurality of memory devices. Such a memory device may be a read-only memory, random access memory, volatile memory, non-volatile memory, static memory, dynamic memory, flash memory, cache memory, and/or any device that stores digital information. While the components of wireless device 120 are shown as being coupled by a particular bus structure, other architectures are likewise possible that include additional data busses and/or direct connectivity between components. Wireless device 120 can include additional components that are not expressly shown.

Likewise, the processing module 141 can be implemented using a microprocessor, micro-controller, digital signal processor, microcomputer, central processing unit, field programmable gate array, programmable logic device, state machine, logic circuitry, analog circuitry, digital circuitry, and/or any device that manipulates signals (analog and/or digital) based on operational instructions that are stored in memory, such as memory 143. Note that when the processing module 141 implements one or more of its functions via a state machine, analog circuitry, digital circuitry, and/or logic circuitry, the memory storing the corresponding operational instructions may be embedded within, or external to, the circuitry comprising the state machine, analog circuitry, digital circuitry, and/or logic circuitry. Further note that, the memory module 143 stores, and the processing module 141 executes, operational instructions corresponding to at least some of the steps and/or functions illustrated herein.

The memory module 143 may be a single memory device or a plurality of memory devices. Such a memory device may be a read-only memory, random access memory, volatile memory, non-volatile memory, static memory, dynamic memory, flash memory, cache memory, and/or any device that stores digital information. While the components of adjunct device 100 are shown as being coupled by a particular bus structure, other architectures are likewise possible that include additional data busses and/or direct connectivity between components. Adjunct device 100 can include additional components that are not expressly shown.

As shown, the adjunct device includes a battery 146 that is separate from the battery of the handheld communication device 110 and can supply power to short-range wireless transceiver 140, processing module 141, user interface 142, memory 143, and device interface 144 in conjunction with a power management circuit, one or more voltage regulators or other supply circuitry. By being separately powered from the handheld communication device 110, the adjunct 100 can operate even if the battery of the handheld communication device is discharged.

Device interface 144 provides an interface between the adjunct device 100 and the handheld communication device 110 and an external device 25, such as a computer or other host device, peripheral or charging unit. As previously discussed in conjunction with FIGS. 1-4, the housing of adjunct device 100 includes a plug, such as plug 26, or other coupling device for connection to the communication port 26' of the handheld communication device 110. In addition, the housing of adjunct device 100 further includes its own communication port, such as communication port 28 or other coupler for connecting to an external device 25. Device interface 144 is coupled to the communication port 28 that operates as a charging port. When adjunct device 100 is connected to an external source of power, such as external device 25, device interface 144 couples a power signal from the external power source to charge the battery 146. In addition, the device interface 144 couples the power signal from the external power source to the communication port of the handheld communication device 110 to charge the battery of the handheld communication device. In this fashion, both the handheld communication device 110 and the adjunct device 100 can be charged at the same time or staged in a priority sequence via logic contained in the adjunct device 110 that, for example, charges the handheld communication device 110 before the adjunct device 100 or vice versa. Further, the handheld communication device 110 can be charged while the devices are still coupled—without removing the adjunct device 100 from the handheld communication device 110.

While the battery 146 is separate from the battery of the handheld communication device 110, in an embodiment of the present invention, the device interface 144 is switchable between an auxiliary power mode and a battery isolation mode. In the battery isolation mode, the device interface 144 decouples the battery 146 from the battery of the handheld communication device 110, for instance, to preserve the charge of battery 146 for operation even if the battery of the handheld communication device 110 is completely or substantially discharged. In the auxiliary power mode, the device interface 144 couples the power from the battery 146 to the handheld communication device 110 via the communication port to charge the battery of the handheld communication device 110. In this fashion, the user of the handheld communication device 110 at or near a discharged state of the handheld communication device battery could opt to draw power from the battery 146. In an embodiment of the present invention, signaling from user interface 142 could be used to switch the device interface 144 between the battery isolation mode and the auxiliary power mode. Alternatively or in addition, signaling received from the handheld communication device via the communication port, or remotely from wireless device 120, could be used to switch the device interface 144 between the battery isolation mode and the auxiliary power mode.

Device interface 144 includes one or more switches, transistors, relays, or other circuitry for selectively directing the flow of power between the external device 25, the battery 146, and the handheld communication device 110 as previously described. In addition, the device interface 144 includes one or more signal paths, buffers or other circuitry to couple communications between the communication port of the adjunct device 110 and the communication port of the handheld communication device 110 to pass through communications between the handheld communication device 110 and an external device 25. In addition, the device interface 144 can send and receive data from the handheld communication device 110 for communication between the adjunct device 100 and handheld communication device 110.

Figure 5:
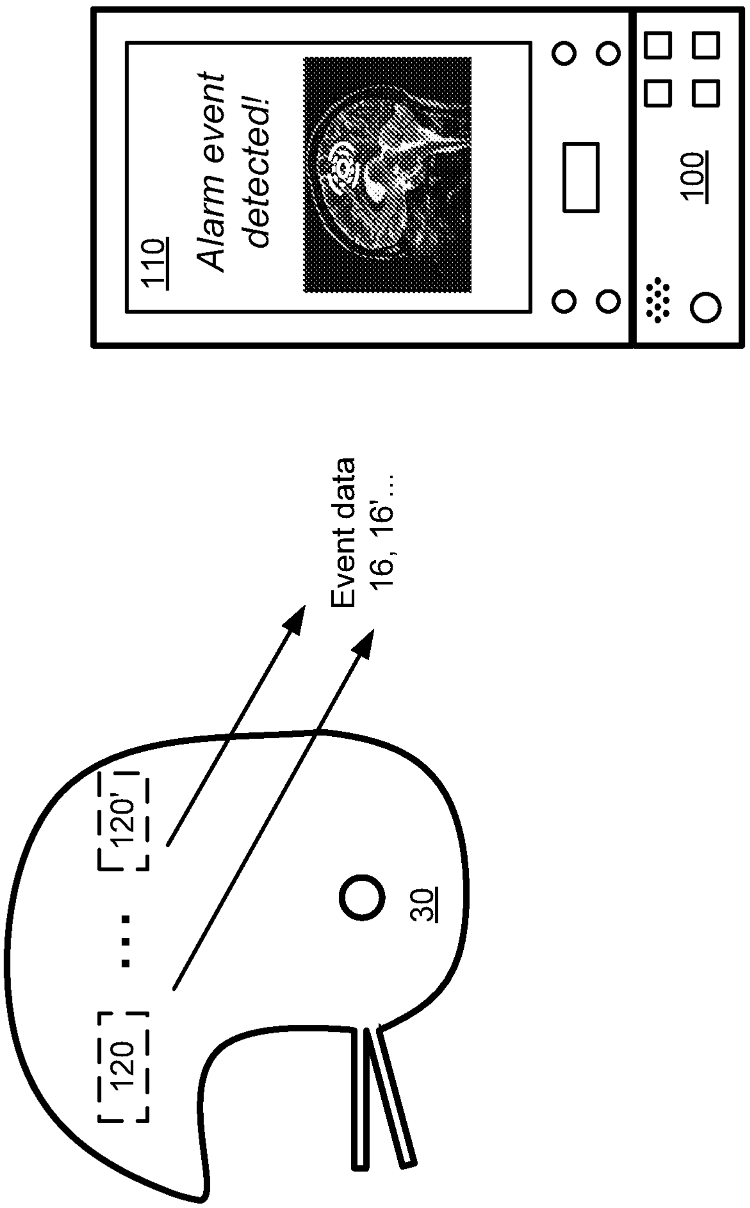
FIG. 5 presents a pictorial representation of a system for monitoring protective headgear in accordance with an embodiment of the present invention.

FIG. 5 presents a pictorial representation of a system for monitoring protective headgear in accordance with an embodiment of the present invention. In particular, an embodiment is presented that includes elements that have been previously described in conjunction with FIG. 1 and are referred to by common reference numerals. In this embodiment however, protective headgear 30 includes a plurality of wireless devices 120 that are designated as (120, 120' . . . ). Each of the wireless devices (120, 120' . . . ) is capable of operating independently and generating event data (16, 16' . . . ) in response to the motion the corresponding sensor modules of the respective wireless devices (120, 120' . . . ).

In operation, event data (16, 16' . . . ) is generated by wireless devices (120 and/or 120' . . . ) in response to an impact to the protective headgear 30. The event data (16, 16' . . . ) is transmitted to the adjunct device 100 that transfers the event data (16, 16' . . . ) to the handheld communication device 110 via the communication port of the handheld communication device 110. The communication device executes an application to further process the event data (16, 16' . . . ) to display a simulation of the head of the wearer of the protective headgear 30 as a result of the impact. The presence of multiple wireless devices (120, 120' . . . ) with a corresponding plurality of separate sensor modules 132 allow more comprehensive modeling of the impact by the protective headgear monitoring application.

Figure 6:
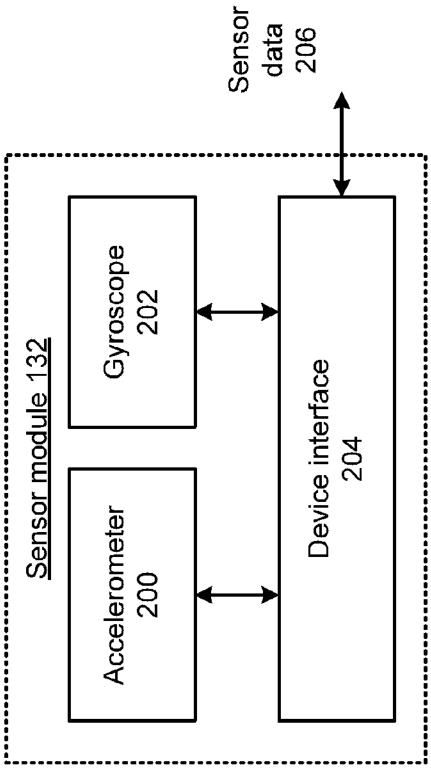
FIG. 6 presents a schematic block diagram of a sensor module 132 in accordance with an embodiment of the present invention.

FIG. 6 presents a schematic block diagram of a sensor module 132 in accordance with an embodiment of the present invention. As shown, sensor module 132 includes an accelerometer 200, a gyroscope 202 and a device interface 204 and generates sensor data 206 that includes both linear acceleration data and rotational acceleration data. The accelerometer 200 can include a piezoresistive accelerometer, piezoelectric accelerometer, capacitive accelerometer, a quantum tunneling accelerometer, a micro electro-mechanical system (MEMS) accelerometer or other accelerometer. In operation, accelerometer 200 is coupled to the protective headgear 30 and responds to acceleration of the protective headgear along a plurality of translational axes and generates linear acceleration data that indicates the acceleration of the protective headgear along 1, 2 or 3 axes such as an x axis, y axis and z axis. Similarly, gyroscope 202 responds to acceleration of the protective headgear along a plurality of axes such as a roll axis, pitch axis and yaw axis and wherein the rotational acceleration data indicates the acceleration of the protective headgear along the plurality of axes. Gyroscope 202 can be implemented via a vibrating element gyroscope, a MEMS gyroscope or other gyroscopic sensor.

The device interface 204 includes device drivers for selectively driving the accelerometer 200 and/or gyroscope 202 and an analog to digital convertor for generating sensor data 206 in response to analog signaling generated by the accelerometer 200 and gyroscope 202. While shown as a separate device, the functionality of device interface 204 can be included in the accelerometer 200 and/or the gyroscope 202.

The use of both an accelerometer and a gyroscope in each sensor module (referred to as a pad) removes the need for a large number of pads. This is partly accomplished by providing both linear and angular acceleration output, and can further be aided by constraining the interpretation of sensor outputs to be consistent with a physical model of the system—which may include the helmet, neck bones and musculature, skull, cerebral fluid, and brain. While only one sensor pad is required when coupled with the physical model of the head, adding multiple sensor pads allows us to account for some types of measurement and modeling errors.

Figure 7:
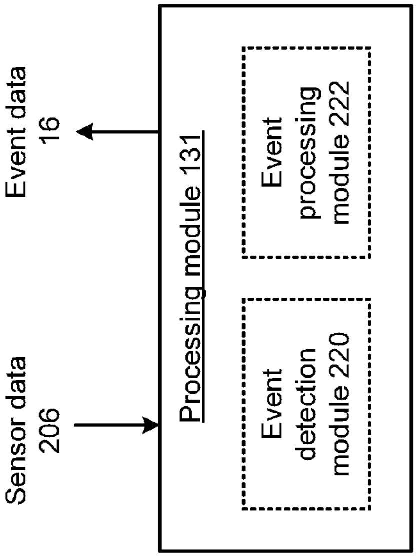
FIG. 7 presents a schematic block diagram of a processing module 131 in accordance with an embodiment of the present invention.

FIG. 7 presents a schematic block diagram of a processing module 131 in accordance with an embodiment of the present invention. As shown, device processing module 131 includes an event detection module 220 and an event processing module 222. The event detection module 220 and event processing module 222 can each be implemented as independent or shared hardware, firmware or software, depending on the implementation of processing module 131. The event detection module 220 analyzes the sensor data 206 and triggers the generation of the event data in response to detection of an event in the sensor data 206.

While some prior art systems judge impact merely based on acceleration, acceleration alone does not tell the whole story. For example, quickly striking a sensor pad with a ballpoint pen can generate acceleration values in the 200 to 300 G range excess of 100 G's for a short time, but this type of impact would hardly be considered dangerous. This type of analysis does not fully account for mass or momentum. Impact measurement is more about energy dissipation rates, or power and/or peak power, potential applied in an oscillating fashion, that is delivered to the head during an impact event. In an embodiment of the present invention, the event processing module 222 analyzes the sensor data 206 to generate event data 16 that include power data that is calculated based on a function of velocity data and acceleration data as a function of time.

For example, consider the example where the sensor module 132 includes a three-axis accelerometer and a three axis gyroscope and wherein sensor data 206 is represented by an acceleration vector A(t), where:

$$A(t)=(\ddot{x}_1,\ddot{x}_2,\ddot{x}_3)$$

And where, $\ddot{x}_i$ is the linear acceleration along the ith axis.

It should be noted that acceleration, A(t), referred above, is raw acceleration from all sources (including gravitational acceleration) and not simply acceleration due to an impact event, exclusive of gravitational acceleration. The quantity a(t) a calibrated event acceleration, which removes the acceleration of gravity, may be defined as follows:

$$a(t)=A(t)C-G(t)$$

Where: G(t) expresses the pull of gravity on the accelerometer, and C is a matrix containing static linear calibration values for each axis of the accelerometer. It should also be understood that the linear calibration matrix C could be replaced by a non-linear function or by a table of values expressing a linear, non-linear function, or non-static calibration.

As shown above, the direction of gravity can be used to more accurately calculate all acceleration dependent values. The starting direction of gravity, $G(t_o)$ at time $t_o$, from the 3-axis accelerometer during a quiescent period, can be used to calculate the direction of gravity throughout an impact event using the 3-axis gyroscope as follows:

$$\phi(t)=\int w(t)dt$$

Where ϕ(t) represents the change in orientation over the integral (in polar coordinates). The angular acceleration $a_a(t)$, can be determined based on $$a_a(t)=\partial/\partial t[w(t)]$$

where w(t) is calibrated angular velocity from the gyroscope 202. The direction of gravity G(t) can be found based on:

$$G(t)=G(t_o)+\mathrm{rect}[\phi(t)]$$

High-g accelerometers may not be sensitive enough to accurately determine the direction of gravity, so a low-g sensor can be employed. On the other hand, expected impact events may exceed the range of a low-g sensor, necessitating a high-g sensor. In an embodiment of the invention, accelerometer 200 includes both a low-g accelerometer, a high-g accelerometer. The low-g accelerometer portion of accelerometer 200 can be employed to determine the direction of gravity as follows. Sensor data is organized into windows with defined start and end times. Sample windows start when the accelerometer 200 and gyroscope 202 are simultaneously quiescent. The sample windows continue when one or more threshold events occur, and end when the gyroscope 202 and accelerometer 200 are simultaneously quiescent a second time. Note the end of one sample window may act as the start of another.

In this embodiment, the low-g portion of accelerometer 200 accurately indicates its orientation with respect to gravity only during quiescent or near quiescent periods, which by definition occur at the start and end of a sample window. If we take $G(t_o)$ to be the average orientation of the low-g sensor at the window start, this term in combination with the calibrated gyro output w(t), can be used to calculate the orientation of gravity throughout the sample window. In a similar fashion, the calculated orientation of gravity at the end of the window, can be compared to the measured value with the difference being used for error detection and correction.

A number of tests for quiescence may be employed. A simple test is when a predetermined number of consecutive samples of the low-g portion of accelerometer 200 have an average norm, n(t), that is approximately equal to 1 g where $$n(t)=|a(t)|$$

For example, a quiescent state is indicated where a consecutive number of samples satisfy the condition:

$$1-e<n(t)<1+e$$

where e represents a tolerance.

Other more robust tests may be employed, for example, where all sensors and all axes must be simultaneously quiescent, as dynamically determined according to some test of statistical significance, whose individual estimated statistics meet one or more criteria, such as the norm of the estimated statistics of the low-g sensor not exceeding 1+e.

In another embodiment of the present invention, the event detection module 220 analyzes the sensor data by generating aggregate acceleration data from the sensor data 206 and comparing the aggregate acceleration data to an acceleration threshold. Event detection module 220 determines an event window that indicates an event time period that spans the event $t_o \le t \le t_f$, based on comparing the aggregate acceleration data to an acceleration threshold. The event detection module 220 triggers the generation of the event data 16 by the event processing module 222, based on this event window. In particular, the event detection module 220 triggers the event processing module 222 to begin generating the event data 16 after the event window ends. The event processing module 222 generates the event data 16 by analyzing the sensor data 206 corresponding to the event window determined by the event detection module 220.

Considering again the example where the sensor module 132 includes a three-axis accelerometer and a three axis gyroscope and wherein sensor data 206 includes a vector B of translational acceleration and angular velocity, where:

$$B=(\ddot{x}_1,\ddot{x}_2,\ddot{x}_3,\dot{\theta}_1,\dot{\theta}_2,\dot{\theta}_3)$$

The event detection module 220 generates an aggregate acceleration and aggregate angular velocity as, for example, the norm of the vector B, and determines the event window $t_1 \le t \le t_2$, as the time period where $|B| \ge T_a$, where $T_a$ represents an aggregate threshold. It should be noted that while a single aggregate threshold 212 is described above, two different thresholds could be employed to implement hysteresis in the generation of the event window. Further while the vector norm is used as a measure of aggregate acceleration and angular velocity, a vector magnitude, or other vector or scalar metrics could be similarly employed. In addition, while event processing module 222 is described as being implemented in the processing module 131 of the wireless device 120, in a further embodiment of the present invention, the event detection module 220 can trigger the generation of event data 16 that merely includes the sensor data 206 during the time window and the functionality of event processing module 222 can be implemented in conjunction with a processing device of the handheld communication device 110 in conjunction with the protective headgear monitoring application.

A portion of the total energy generated at impact is not easily calculated from accelerometer data—that portion which produces no bulk motion, and instead is dissipated within the helmet's structure or mechanically transferred to objects or surfaces in contact with the helmet. So long as no structural limit of the helmet is exceeded, such impact energy can be ignored. Consider the example where a helmet is in contact with the ground and the impact produces no motion of the helmet.

That portion of impact energy producing motion, perhaps violent motion of the helmet, is of great interest from a personal injury standpoint. Energy of motion, or kinetic energy, is calculable from accelerometer data. The rate at which kinetic energy is imparted and then dissipated, or power, is a consistent indicator of the potential for brain injury from an impact event.

In an embodiment of the present invention, power data can be determined based on a calculation of the mechanical power corresponding to an impact event. The mechanical power P(t) represents a rate of force applied through a distance and over an event window $t_1 \le t \le t_2$, and where force is calculated as the product of mass, m, and acceleration as follows:

$$\begin{aligned} P(t) &= m\frac{\partial}{\partial t}\left[a(t)\int_{t_1}^{t_2}\int a(t)\,dt\,dt\right] \\ &= m[a(t)v(t)] \end{aligned}$$

Mass in this case is the estimated mass of the entire system including the head and the protective headgear, and where the velocity v(t) can be found based on:

$$\begin{aligned} v(t) &= \int a(t)\,dt \\ &= (\dot{x}_1, \dot{x}_2, \dot{x}_3) \end{aligned}$$

This form of event data 16 more closely represents power of impact to the protective headgear.

In other embodiments, power data, different from mechanical power can be employed in favor of other power-related data that is not strictly dependent on the mass of the head helmet system. As previously discussed, the mechanical power can be expressed as:

$$P(t)=m[+a(t)v(t)]$$

The mass m can be expressed in terms of the volume u and average density d of the head and helmet system as:

$$m=du$$

Power data can be based on a power diffusion q(t) expressed as follows:

$$q(t) = \frac{P(t)}{u} = d[a(t)v(t)]$$

Considering that the average density of the head helmet system is a constant, the power diffusion q(t) is proportional to a related power diffusion term Q(t) that is calculated as:

$$Q(t) = \frac{P(t)}{m} = [a(t)v(t)]$$

Expressing the kinetics of an impact based on either of the power diffusion terms q(t) or Q(t) allows the power data to be computed without accounting for the mass of the entire system, providing a normalized metric useful in assessing the severity of an impact event. While power has been described above in linear-translational terms, it is possible to develop power metrics in rotational-torsional terms. Any of the power terms P(t), q(t), Q(t), previously described in terms of only linear (translational) motion can be calculated instead in terms of rotational motion or a combination of linear and rotational motion. For example, rotational kinetics, such as the quantity β(t) presented below, can be a factor in assessing the potential for brain injury and can, in particular, be considered either alone or in combination with translational kinetics.

$$\beta(t)=a_a(t)w(t)$$

It follows that the event data 16 can include a(t), v(t), x(t), q(t), Q(t), $a_a(t)$, w(t), ϕ(t), β(t), along with similar quantities, any intermediate calculations or raw data used to calculate any of these quantities. In particular a(t), v(t), x(t), q(t), Q(t), $a_a(t)$, w(t), ϕ(t), β(t) and other measured or calculated quantities can be employed in a number of useful ways. Such as applying individual or compound thresholds to determine if an injury event may have occurred, or in preparing useful simulations and displays, involving animations and/or color maps to express impact severity or to provide educational displays to increase awareness among coaches, players, medical personnel and parents in a sports setting, and to others in the context of law enforcement, industrial applications, and other uses of protective headgear 30. In particular event data 16 can also include a system status such as a battery status, low battery indicator, system ready indicator, system not ready indicator or other status.

It should also be noted that event data 16 can include merely an alarm indication in a failsafe mode of operation. For example in circumstances where an event window begins, however due to low power, a fault condition or other error, particular values of a(t), v(t), x(t), q(t), Q(t), $a_a(t)$, w(t), ϕ(t) cannot be calculated or are deemed to be unreliably calculated due to an internal error detection routine, the event data 16 can merely include an alarm signal that is sent to adjunct device 100 to trigger an alarm in the handheld communication device 110 of a potential high impact event that cannot be analyzed. Further, event data 16 can include periodic status transmissions or other transmission to the adjunct device 100 indicating that the wireless device 120 is operating normally. In the absence of receiving one or more such periodic transmissions, the adjunct device 100 can trigger an alarm indicating that a wireless device has failed to check in and may be out of range, out of battery power or otherwise in a non-operational state.

Figure 8:
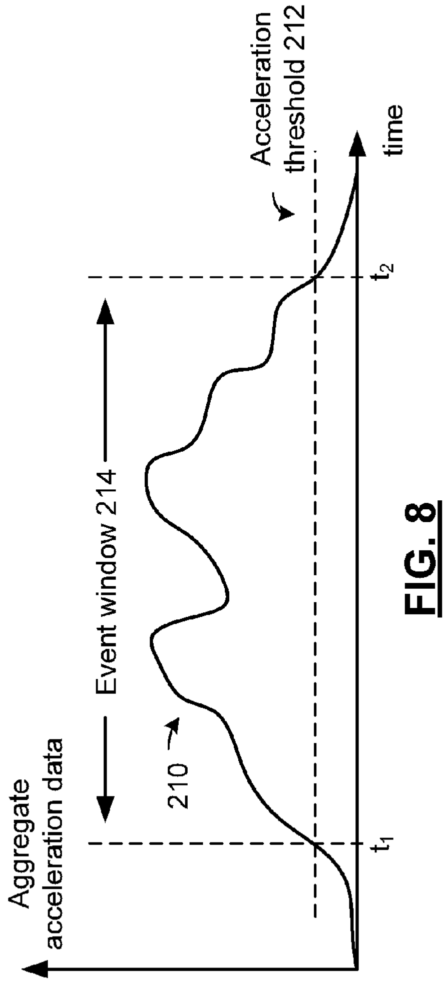
FIG. 8 presents a graphical representation of aggregate acceleration data as a function of time in accordance with an embodiment of the present invention.

FIG. 8 presents a graphical representation of aggregate acceleration data as a function of time in accordance with an embodiment of the present invention. In particular, the line 210 represents an example of aggregate acceleration data as a function of time. When the line 210 first exceeds the acceleration threshold 212 at time $t_1$, the event detection module 220 detects the beginning of an event. The event window 214 is determined based on when the aggregate acceleration next falls below the acceleration threshold 212 at time $t_2$.

As discussed in conjunction with FIG. 7, an event window is determined, for example, based on the time period between two quiescent periods. The event detection module 220 triggers the generation of the event data 16 by the event processing module 222, based on this event window. For example, the event detection module 220 triggers the event processing module 222 to begin generating the event data 16 during the event window and triggers transmitting the event data 16 either during the event window or after the event window ends. The event processing module 222 generates the event data 16 by analyzing the sensor data 206 corresponding to the event window determined by the event detection module 220.

Figure 10:
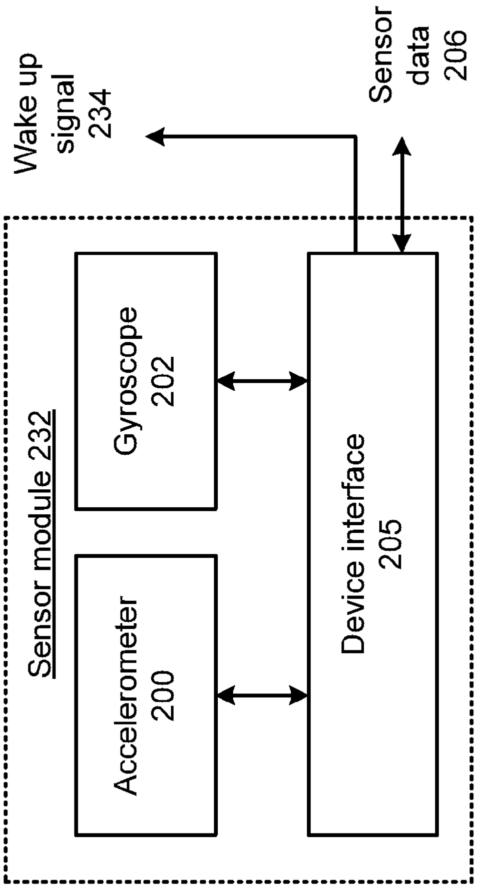
FIG. 10 presents a schematic block diagram of a sensor module 232 in accordance with an embodiment of the present invention.
Figure 9:
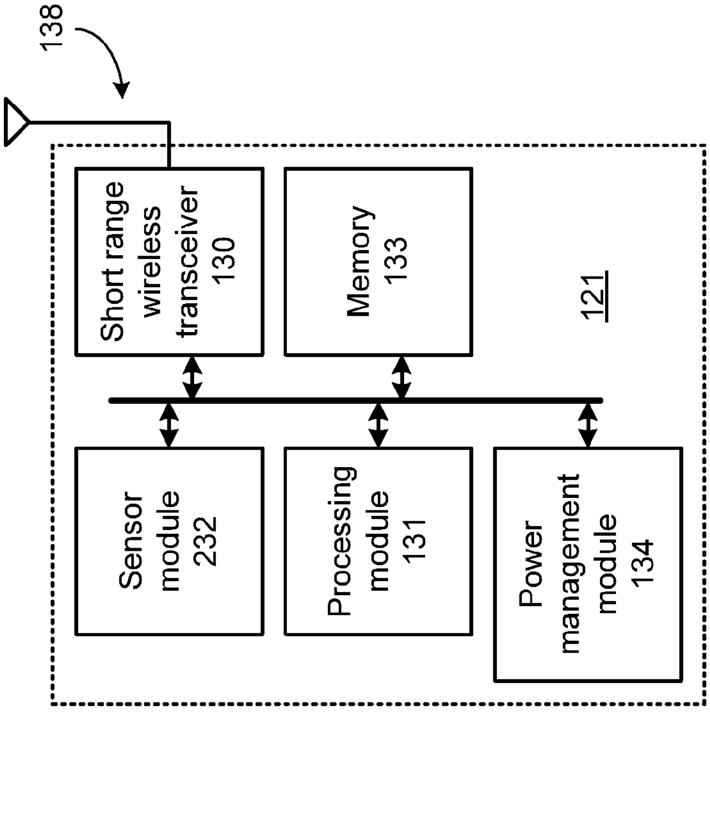
FIG. 9 presents a schematic block diagram of a wireless device 121 in accordance with an embodiment of the present invention.

FIG. 9 presents a schematic block diagram of a wireless device 121 in accordance with an embodiment of the present invention and FIG. 10 presents a schematic block diagram of a sensor module 232 in accordance with an embodiment of the present invention. Wireless device 121 includes many common elements of wireless device 120 that are referred to by common reference numerals and can be used in place of wireless device 120 in any of the embodiments described therewith. Wireless device 121 includes a sensor module 232 that includes a device interface 205 that operates in a similar fashion to device interface 204, yet further generates a wake-up signal 234. Wireless device 121 includes a power management module 134 that selectively powers the short-range transmitter/transceiver 130, the processing module 131 and optionally memory 133 in response to the wake-up signal. This saves power and extends battery life of wireless device 121.

In an embodiment of the present invention, the sensor module 232 generates the wake-up signal 234 when an acceleration signal from the accelerometer 200 and/or the angular velocity from the gyroscope 202 compares favorably to a signal threshold. Considering again the example where the sensor module 132 includes a three-axis accelerometer and a three axis gyroscope and wherein sensor data 206 is represented by an aggregate acceleration angular velocity vector B, where:

$$B=(\ddot{x}_1,\ddot{x}_2,\ddot{x}_3,\dot{\theta}_1,\dot{\theta}_2,\dot{\theta}_3)$$

The device interface 205 includes hardware, software or firmware that generates an aggregate acceleration as, for example, the norm of the vector B, and generates wake-up signal 234 in response to event where $|B|$ first exceeds $T_s$, where $T_s$ represents a signal threshold. In an embodiment the signal threshold $T_s=T_a$, however other values can be employed. For example, a value of $T_s=T_a-k$, can be employed to provide a more sensitive value of the wake-up signal and further to trigger wake-up of the components of the wireless device 121 prior to the beginning of the event window. It should also be noted that a wake-up signal 234 can be generated based on the end of a quiescent period as described in conjunction with FIG. 7.

In an embodiment of the present invention, the device interface 205 directly monitors the outputs of the accelerometer 200 and/or gyroscope 202. In this case, device interface 205 generates the sensor data 206 only in response to the wake-up signal 234. In this fashion, the sensor data 206 is only generated, when needed. In another embodiment, device interface generates sensor data 206 continuously and generates wake-up signal 234 based on an analysis of the sensor data 206. While the device interface 205 has been described in the example above as using an aggregate of all the acceleration components to generate a wake-up signal, in a further embodiment, the device interface 205 may only monitor a limited subset of all axes of linear and rotational acceleration in order to wake-up the device. In this fashion, only some limited sensor functionality need be powered continuously—saving additional power.

While described above in terms of the use of accelerometer 200 or gyroscope 202 as the ultimate source of sensor data for the wake up signal, in another embodiment of the present invention, the wake-up signal is generated by a separate wake-up sensor, such as a kinetic senor, piezoelectric device or other device that generates a wake-up signal in response to the beginning of an impact event.

Figure 11:
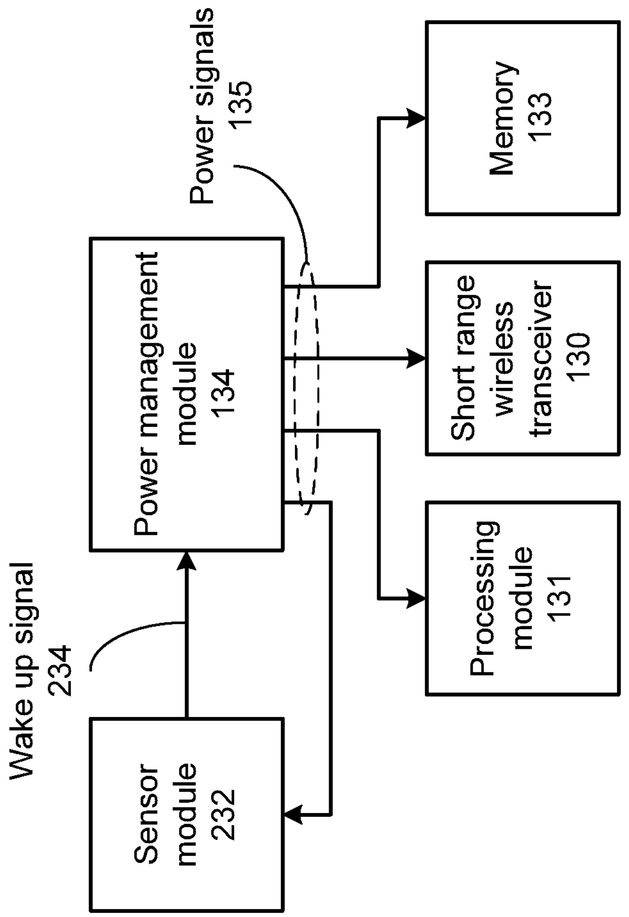
FIG. 11 presents a schematic block diagram of a power management module 134 in accordance with an embodiment of the present invention.

FIG. 11 presents a schematic block diagram of a power management module 134 in accordance with an embodiment of the present invention. As described in conjunction with FIGS. 9-10, power management module 134 selectively powers the short-range transmitter/transceiver 130, the processing module 131 and optionally memory 133 in response to the wake-up signal. Power management module generates a plurality of power signals 135 for powering these devices when triggered by the wake-up signal 234.

As shown, the power management module 134 further generates an additional power signal 135 for powering the sensor module 232 and optionally increased the power generated in response to the wake-up signal 234. In the example where device interface 205 operates with limited functionality prior to generation of the wake-up signal 234, the power is increased to sensor module 232 in order to power the devices necessary to drive the full range of sensors and further to generate sensor data 206. This can include selectively powering an analog to digital converted included in device interface 205, only in response to the wake-up signal 234.

Figure 12:
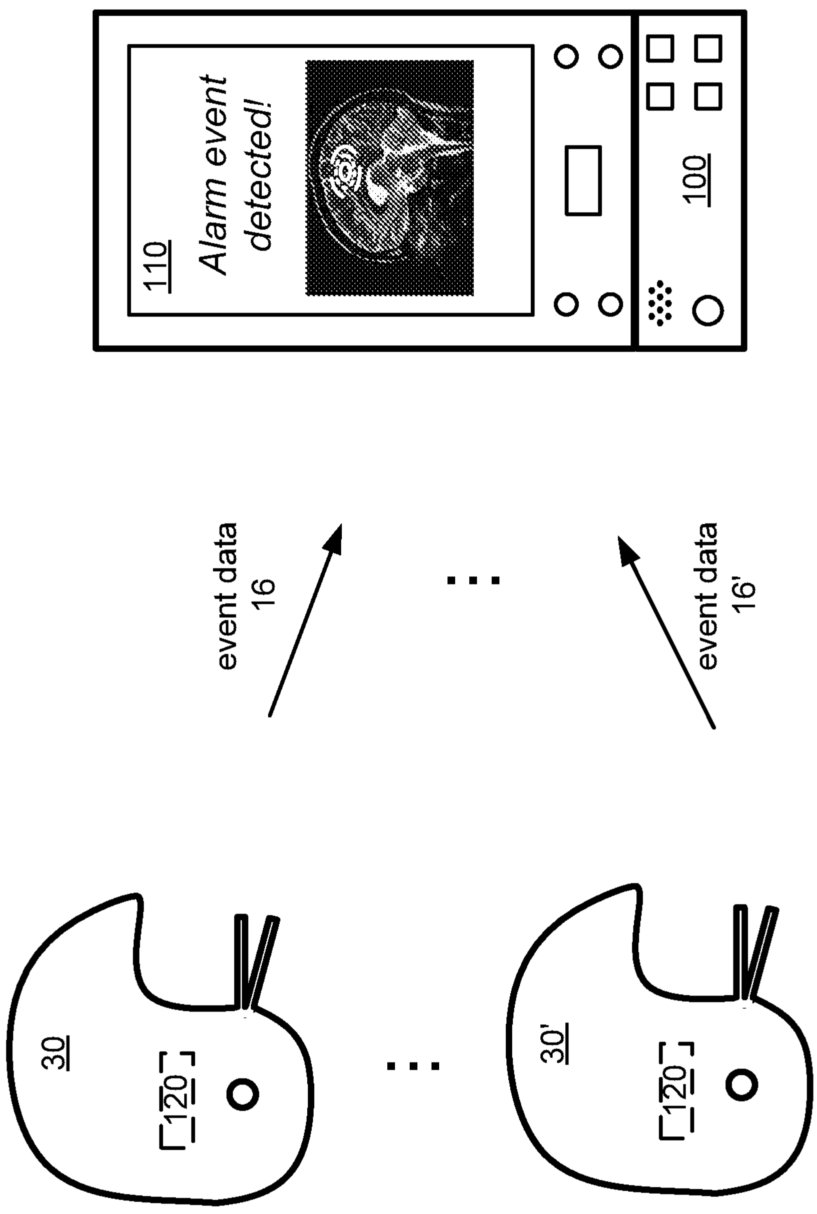
FIG. 12 presents a pictorial representation of a system for monitoring protective headgear in accordance with an embodiment of the present invention.

FIG. 12 presents a pictorial representation of a system for monitoring protective headgear in accordance with an embodiment of the present invention. In particular, a system is shown that operates in conjunction with any of the embodiments presented in conjunction with FIGS. 1-11. In this embodiment however, the adjunct device 100 and handheld communication device operate to monitor a plurality of protective headgear 30. Event data (16, 16' . . . ) from any of the plurality of protective headgear (30, 30' . . . ) are received and used by a protective headgear monitoring application of handheld communication device 110. In operation, the application processes the event data (16, 16' . . . ) to, for example, display a simulation of the head and/or brain of the wearer of the protective headgear 30 and/or 30' as a result of an impact.

Figure 13:
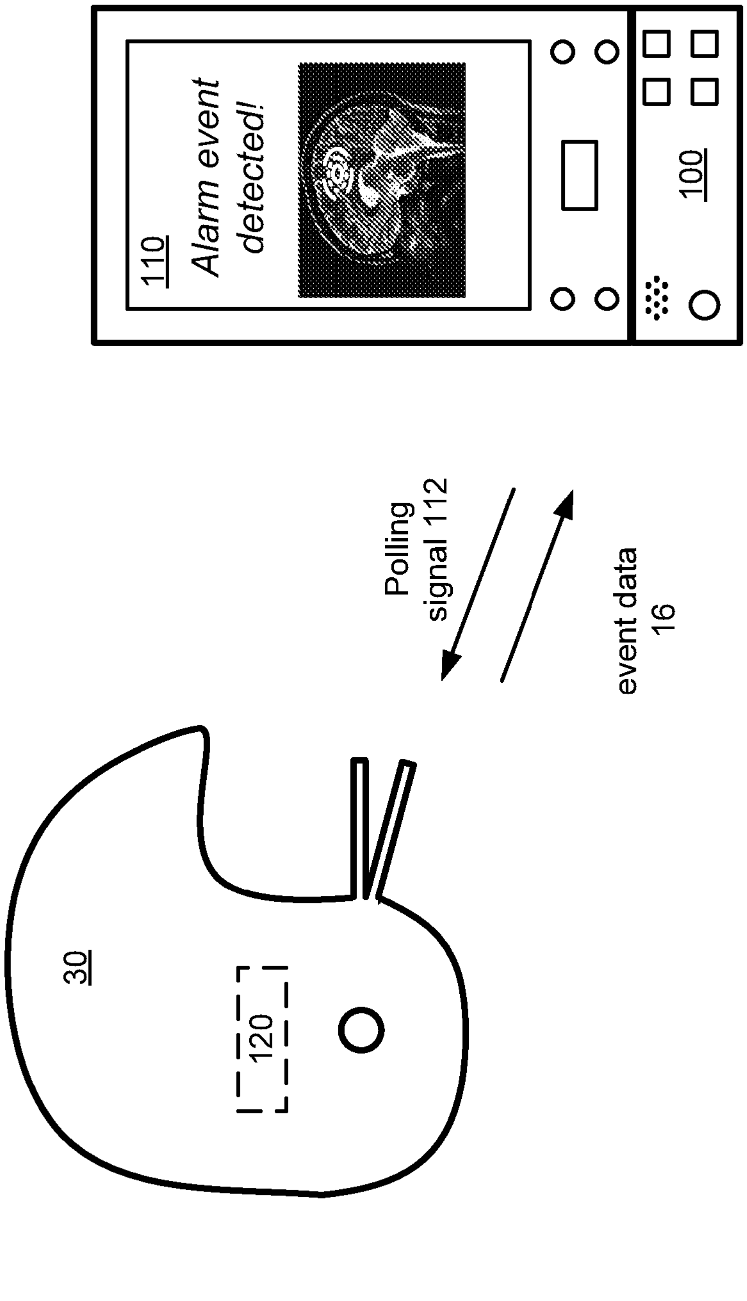
FIG. 13 presents a pictorial representation of a system for monitoring protective headgear in accordance with an embodiment of the present invention.

FIG. 13 presents a pictorial representation of a system for monitoring protective headgear in accordance with an embodiment of the present invention. As previously described, the wireless device 120 can automatically generate event data 16 in response to the detection by the wireless device 120 of an event. In this fashion, event data 16 can be pushed to an adjunct device 100. In this embodiment however, the wireless device 120 receives a polling signal 112 transmitted by adjunct device 110. In response to the polling signal 112, the wireless device 120 generates a wireless signal that contains either event data 16, a system status such as a battery status, system ready indicator, other status or other data.

For example, a parent watching a football game in the stands notices a blow to the helmet of their child. The parent launches a protective headgear monitoring application of the handheld communication device 110 that causes adjunct device 100 to emit the polling signal 112. The wireless device 120 responds to polling signal 112 by generating a wireless signal that is transmitted back to adjunct device 100. The polling signal can include event data 16. In this fashion, the event data 16 can be generated and or transmitted by wireless device 120 on demand from the user of the handheld communication device 110.

As mentioned above, other types of data can be transmitted by wireless device 120 in response to the polling signal 112. In another example, the wireless device 120 can monitor its remaining battery life and transmit battery life data to the adjunct device 100 in response to the polling signal 112. In this fashion, the user of handheld communication device 110 can easily monitor battery life of one or more wireless devices 120 and charge them when necessary—such as prior to a game or other use of protective headgear 30. While battery life is described above in a pull fashion, a low battery indication from a wireless device 120 can also be pushed to the adjunct device 100, even in circumstances where other event data is pulled from the wireless device 120.

In a further example, the wireless device 120 can emit a location beacon or other signal in response to the polling signal 112 to aid the user of handheld communication device 120 in locating the protective headgear 30. In this embodiment, the protective headgear monitoring application of handheld communication device 110 can include an equipment location software module that, for example presents a special screen that allows the user to monitor the signal strength and/or the directionality of the location signal, to assist the user in homing in on the location of the protective headgear 30. In this embodiment, the wireless device 120, adjunct device 100 and/or handheld communication device 100 includes one or more of the functions and features described in the U.S. Published Application number 2011/021047, entitled "SYSTEM AND WIRELESS DEVICE FOR LOCATING A REMOTE OBJECT", the contents of which are incorporated herein by reference thereto.

Figure 14:
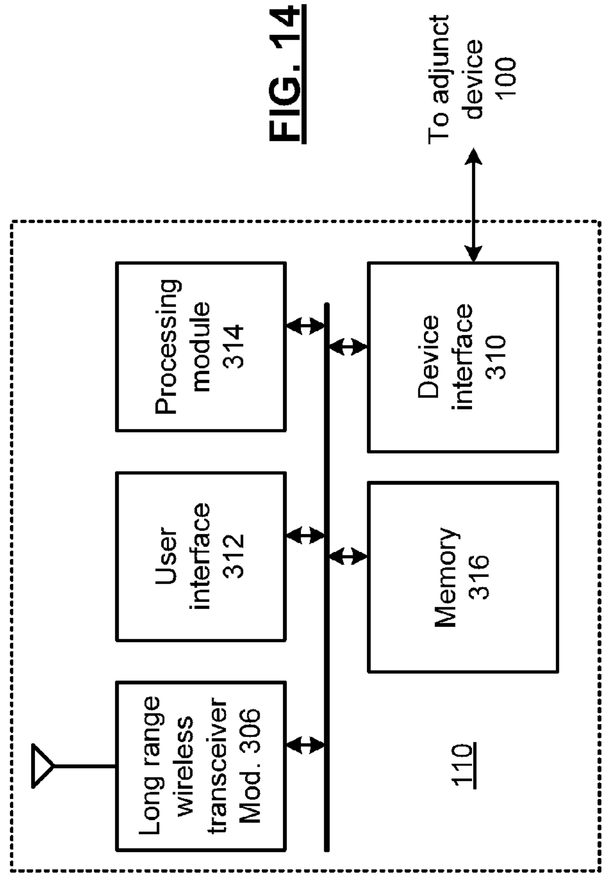
FIG. 14 presents a schematic block diagram of a handheld wireless device 110 in accordance with an embodiment of the present invention.

FIG. 14 presents a schematic block diagram of a handheld wireless device 110 in accordance with an embodiment of the present invention. Handheld communication device 110 includes long range wireless transceiver module 306, such as a wireless telephony receiver for communicating voice and/or data signals in conjunction with a handheld communication device network, wireless local area network or other wireless network. Handheld communication device 110 also includes a device interface 310 for connecting to the adjunct device 100 on either a wired or wireless basis, as previously described. In particular, the device interface 310 includes a communication port that receives the event data 16, 16' . . . from one or more wireless devices 120 coupled to one or more protective headgear 30, 30' . . . via an adjunct device 100 connected to the communication port.

In addition, handheld communication device 300 includes a user interface 312 that include one or more pushbuttons such as a keypad or other buttons, a touch screen or other display screen, a microphone, speaker, headphone port or other audio port, a thumbwheel, touch pad and/or other user interface device. User interface 312 includes the user interface devices ascribed to handheld communication device 110.

Handheld communication device 110 includes a processing module 314 that operates in conjunction with memory 316 to execute a plurality of applications including a wireless telephony application and other general applications of the handheld communication device and other specific applications such as the protective headgear monitoring described in conjunction with FIGS. 1-13.

The processing module 314 can be implemented using a microprocessor, micro-controller, digital signal processor, microcomputer, central processing unit, field programmable gate array, programmable logic device, state machine, logic circuitry, analog circuitry, digital circuitry, and/or any device that manipulates signals (analog and/or digital) based on operational instructions that are stored in memory, such as memory 316. Note that when the processing module 314 implements one or more of its functions via a state machine, analog circuitry, digital circuitry, and/or logic circuitry, the memory storing the corresponding operational instructions may be embedded within, or external to, the circuitry comprising the state machine, analog circuitry, digital circuitry, and/or logic circuitry. Further note that, the memory module 316 stores, and the processing module 314 executes, operational instructions corresponding to at least some of the steps and/or functions illustrated herein.

The memory module 316 may be a single memory device or a plurality of memory devices. Such a memory device may be a read-only memory, random access memory, volatile memory, non-volatile memory, static memory, dynamic memory, flash memory, cache memory, and/or any device that stores digital information. While the components of handheld communication device 110 are shown as being coupled by a particular bus structure, other architectures are likewise possible that include additional data busses and/or direct connectivity between components. Handheld communication device 110 can include additional components that are not expressly shown.

As previously described, event data 16 is generated by wireless device 120 in response to an impact to the protective headgear 30. The event data 16 is transmitted to the adjunct device 100 that transfers the event data 16 to the handheld communication device 110, either wirelessly or via the communication port of the handheld communication device 110. The handheld communication device 110 executes an application to further process the event data 16 to, for example, display a simulation of the head and/or brain of the wearer of the protective headgear 30 as a result of the impact. Further details regarding the simulation of the impact event are presented in conjunction with FIG. 15 that follows.

Figure 15:
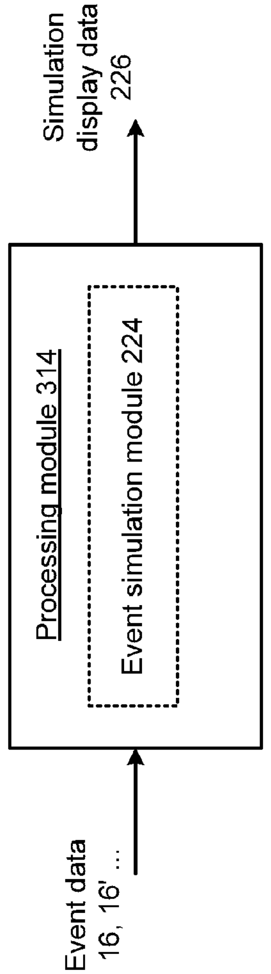
FIG. 15 presents a schematic block diagram of a processing module 314 in accordance with an embodiment of the present invention.

FIG. 15 presents a schematic block diagram of a processing module 314 in accordance with an embodiment of the present invention. In particular processing module 314 executes an event simulation module that processes the event data (16, 16' . . . ) to generate simulation display data 226 that animates the impact to the protective headgear 30. The user interface 312 includes a display device that displays the simulation display data 226. The event simulation module can be included in the protective headgear monitoring application executed by processing module 314 of the handheld communication device 110. The protective headgear monitoring application can be implemented as an article of manufacture that includes a computer readable medium or as other instructions that, when executed by a processing device cause the processing device to implement the functions described herein in conjunction with the other components of the handheld communication device 110. As previously described the protective headgear monitoring application can be an "app" that is downloaded to the handheld communication device 110 via the long range wireless transceiver module 306, a wireless local area network connection or other wired or wireless link.

In an embodiment of the present invention, the event simulation module 224 models a human head that simulates the head of the wearer of the protective headgear (30, 30' . . . ), the shock absorbing capabilities of the protective headgear (30, 30' . . . ) a human skull and/or brain that simulates the skull and brain of the wearer of the protective headgear (30, 30' . . . ). For example, the event simulation module 224 can implement a bulk system model, a lumped parameter system module or other model that accounts for the mass of the head and how its movement is constrained by the joints and musculature the neck. This model allows the event simulation module to account for the way forces and movements are distributed in a bulk way; showing for example, how energy is dissipated over the surface of the brain. The event simulation module can further include a second, more complex model, such as a finite element model or a distributed parameter model that simulates sub-surface displacements/injury to brain matter. In this fashion, power, velocity and/or displacement data either received as event data 16 or calculated locally in response to event data 16 that includes sensor data 206 corresponding to an event can be used to simulate the impact.

In an embodiment of the present invention, the simulation display data 226 includes graphics and video animation to visually communicate the nature and potential extent of the injury caused by an impact event. A depiction of the brain can be animated, showing the entire impact event. Power, velocity and/or other event data 16 are used to drive the animation, while a color map is applied to the surface of the brain to indicate points of high energy dissipation. The simulation display data 226 can also show possible brain impact with the skull as well as the deformation of brain matter as predicted by the second, more complex model.

In addition, to simply providing an animation, the event simulation module 224 can generate an alarm event signal as part of the simulation display data 226. This alarm event signal can be generated when the event simulation module 224 either receives event data 16 regarding any impact that indicates the alarm event directly, or alternatively when the event simulation module 224 determines that an impact has occurred with sufficient force as a cause a possible injury. For example the event simulation module 224 can compare a peak power to an injury threshold and generate the alarm event signal when the peak power exceeds an injury threshold. In the alternative, the event simulation module can analyze the results of the brain or head modeling and determine a potential injury situation and trigger the alarm event signal in response to such a determination. The alarm event signal is used to trigger a visual alarm such as a warning light, banner display or display message and/or an audible alarm such as a tone, alarm sound, buzzer or other audible warning indicator. While the description above includes a single threshold, multiple thresholds can be employed to determine alarm events of greater or lesser severity. Different responses to the alarm event signal can be employed, based on the severity of the alarm event.

In addition to generating a local alarm, the alarm event signal, the event data (16, 16' . . . ) and/or the simulation display data 226 can be sent by the handheld communication device 110 to a remote monitoring station via the wireless telephony transceiver module 206. In this fashion, the event data (16, 16' . . . ) and/or the simulation display data 226 can be subjected to further analysis at a remote facility such as hospital, doctor's office or other remote diagnosis or treatment facility in conjunction with the diagnosis and treatment of the wearer of the protective headgear (30, 30' . . . ) that was the subject of the impact. It should be noted that the transmission of a wireless signal including the event data (16, 16' . . . ) and/or the simulation display data 226 can be either triggered automatically in response to the alarm event signal or triggered manually in response to an indication of the user of the handheld communication device 110, via interaction with the user interface 312.

FIG. 16 presents a pictorial representation of a system for monitoring protective headgear in accordance with an embodiment of the present invention. While many of the prior descriptions of the present invention contained herein focus on functions and features ascribed to an adjunct device operating in conjunction with a handheld communication device, the functions and features of the adjunct device/handheld communication device combination can be implemented in an enhanced handheld communication device that includes structure and functionality drawn from an adjunct device, such as adjunct devices 100. Handheld communication device 300 presents such a device that includes a handheld communication device portion having the standard components of a handheld communication device and an adjunct portion that adds the components necessary to provide the additional functions and features of the adjunct device 100. In summary, handheld communication device 300 includes the structure and functionality of any of the embodiments of handheld communication device 110 and adjunct device 100 to interact with one or more wireless devices 120 included in one more articles or protective headgear 30.

FIG. 17 presents a schematic block diagram of a handheld wireless device 300 in accordance with an embodiment of the present invention. Handheld communication device includes similar elements to handheld communication device 110 that are referred to by common reference numerals. In addition, handheld communication device 300 includes a short range wireless transceiver module 304 that operates in a similar fashion to short range wireless transceiver 140 to provide a device interface to interact with one or more wireless devices 120, to receive event data (16, 16' . . . ) and to transfer this event data to processing module 314 for further analysis.

Figure 18:
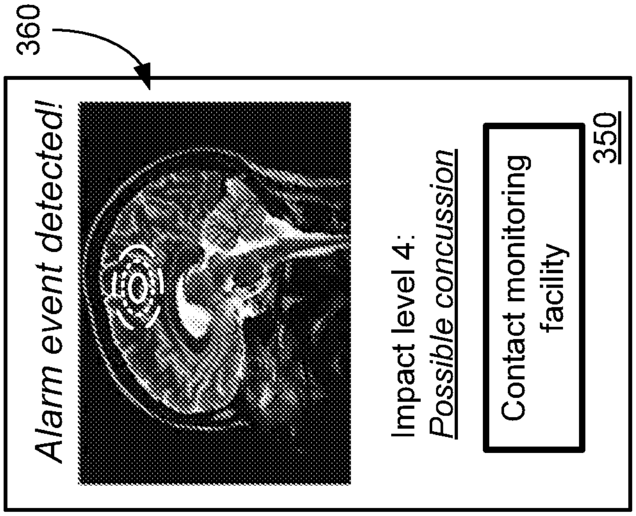
FIG. 18 presents a pictorial representation of a screen display 350 in accordance with an embodiment of the present invention.

FIG. 18 presents a pictorial representation of a screen display 350 in accordance with an embodiment of the present invention. In particular, screen display 350 is shown of simulation display data 226 in accordance with a particular example. In this example, screen display 350 includes a frame 360 of video animation that visually communicates the nature and potential extent of the injury caused by an impact event. A depiction of the brain and skull is animated, showing a particular video frame of the entire impact event. A series of graphical overlays outline regions of high energy dissipation on the surface of or internal to the brain. In this diagram different regions are indicates as to the intensity of energy dissipation based on lines of different styles, however, regions of different colors can likewise be used to provide greater visual contrast.

In addition to the video animation, the simulation display data 226 provides a visual indication of an alarm event by displaying the text, "Alarm event detected!" and further an indication of the level of impact and its possible effect, "Impact level 4: Possible concussion". An interactive portion of the screen display 350 can be selected by the user to initiate the process of contacting a monitoring facility such as hospital, doctor's office or other remote diagnosis or treatment facility.

Figure 19:
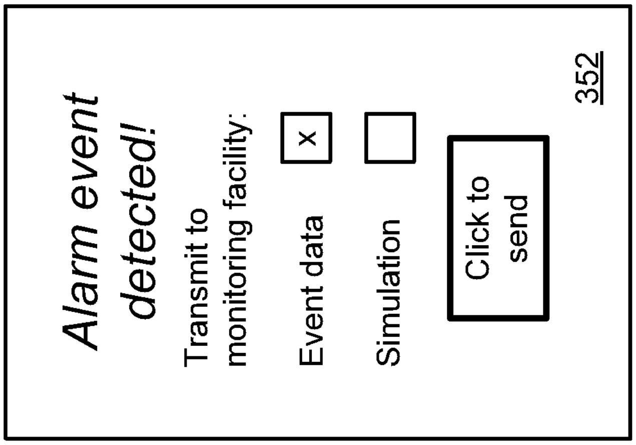
FIG. 19 presents a pictorial representation of a screen display 352 in accordance with an embodiment of the present invention.

FIG. 19 presents a pictorial representation of a screen display 352 in accordance with an embodiment of the present invention. In particular, an example of a follow-up screen is presented in response to the selection by the user to contact a monitoring facility described in conjunction with FIG. 18. In particular, screen display 352 allows the user to select the type of information to be sent to the monitoring facility. In the example shown, the user can select event data, such as event data (16, 16' . . . ) and/or a full simulation, such as simulation display data 226 or other simulation results to be transmitted to the remote facility. While not expressly shown, the event data and simulation data can be accompanied by information that identifies the user of the handheld communication device, the wearer of the protective headgear that was the subject of the impact event, other identifying data such as address information, physician information, medical insurance information and/or other data. An interactive portion of the screen display 352 can be selected by the user to either store the selected data or used to initiate the transmission of the selected data to a monitoring facility such as hospital, doctor's office or other remote diagnosis or treatment facility.

Figure 20:
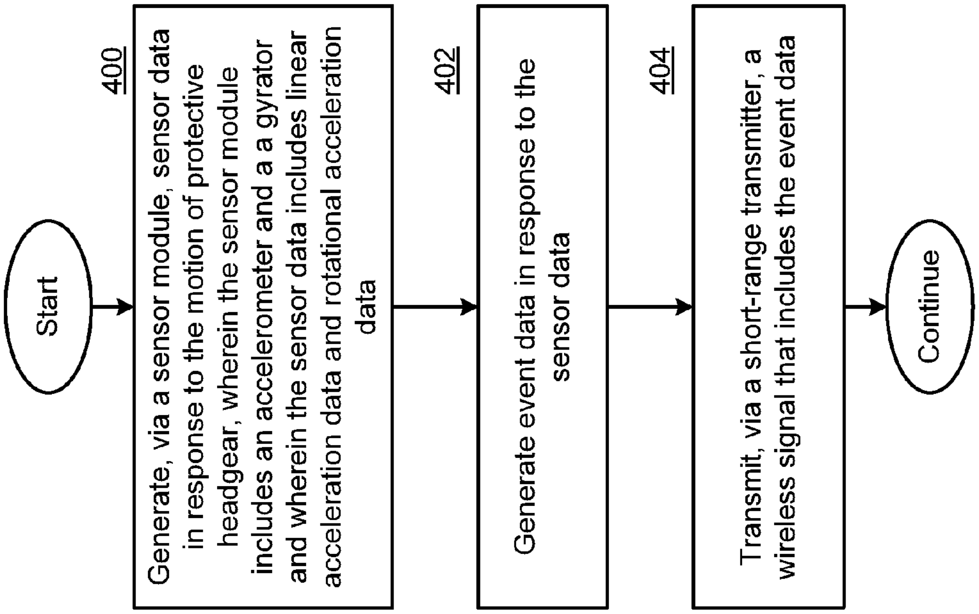
FIG. 20 presents a flowchart representation of a method in accordance with an embodiment of the present invention.

FIG. 20 presents a flowchart representation of a method in accordance with an embodiment of the present invention. In particular, a method is shown for use in conjunction with one or more functions and features described in conjunction with FIGS. 1-19. In step 400, sensor data is generated, via a sensor module, in response to motion of protective headgear, wherein the sensor module includes an accelerometer and a gyroscope and wherein the sensor data includes linear acceleration data and rotational velocity data. In step 402, event data is generated in response to the sensor data. In step 404, a wireless signal that includes the event data is transmitted via a short-range wireless transmitter.

In an embodiment of the present invention, the wireless signal is transmitted to an adjunct device that is coupled to a handheld communication device for processing of the event data by the handheld communication device. The accelerometer responds to acceleration of the protective headgear along a plurality of axes and the linear acceleration data indicates the acceleration of the protective headgear along the plurality of axes. In addition, the gyroscope responds to angular velocities of the protective headgear along a plurality of axes and the rotational velocity data indicates the velocity of the protective headgear along the plurality of axes.

Figure 21:
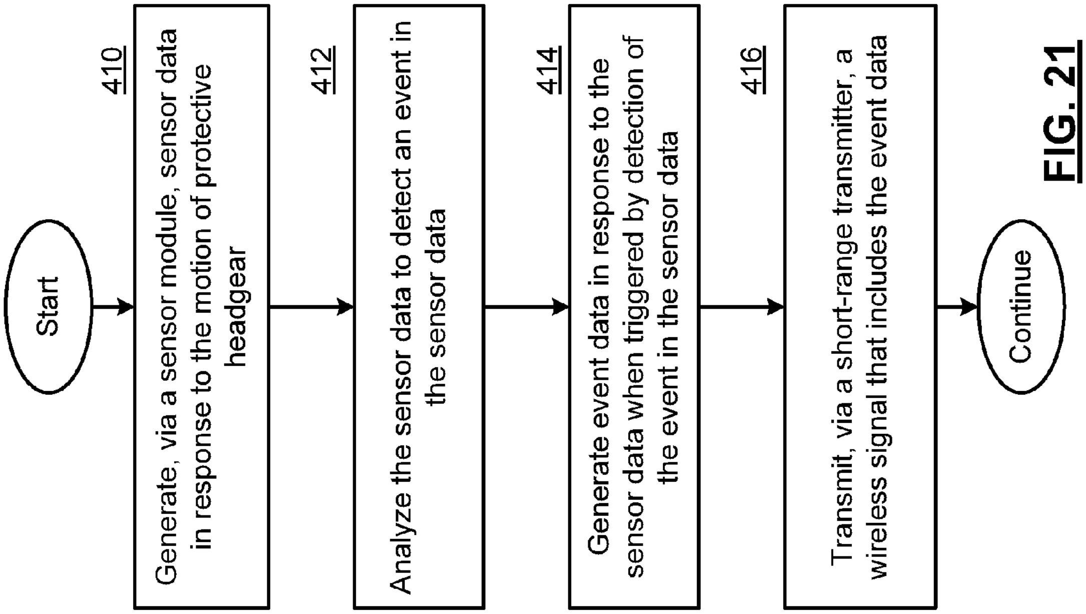
FIG. 21 presents a flowchart representation of a method in accordance with an embodiment of the present invention.

FIG. 21 presents a flowchart representation of a method in accordance with an embodiment of the present invention. In particular, a method is shown for use in conjunction with one or more functions and features described in conjunction with FIGS. 1-20. In step 410, sensor data is generated, via a sensor module, in response to motion of protective headgear. In step 412, the sensor data is analyzed to detect an event in the sensor data. In step 414, event data is generated in response to the sensor data when triggered by detection of the event in the sensor data. In step 416, a wireless signal that includes the event data is transmitted via a short-range wireless transmitter.

In an embodiment of the present invention, the wireless signal is transmitted to an adjunct device that is coupled to a handheld communication device for processing of the event data by the handheld communication device. Step 412 can include generating aggregate acceleration data from the sensor data; comparing the aggregate acceleration data to an acceleration threshold; and determining an event window that indicates an event time period based on the comparing of the aggregate acceleration data to the acceleration threshold. Step 414 can be triggered based on the event window, such as after the event window ends and the event data can be generated in step 414 in response to the sensor data corresponding to the event window.

Figure 22:
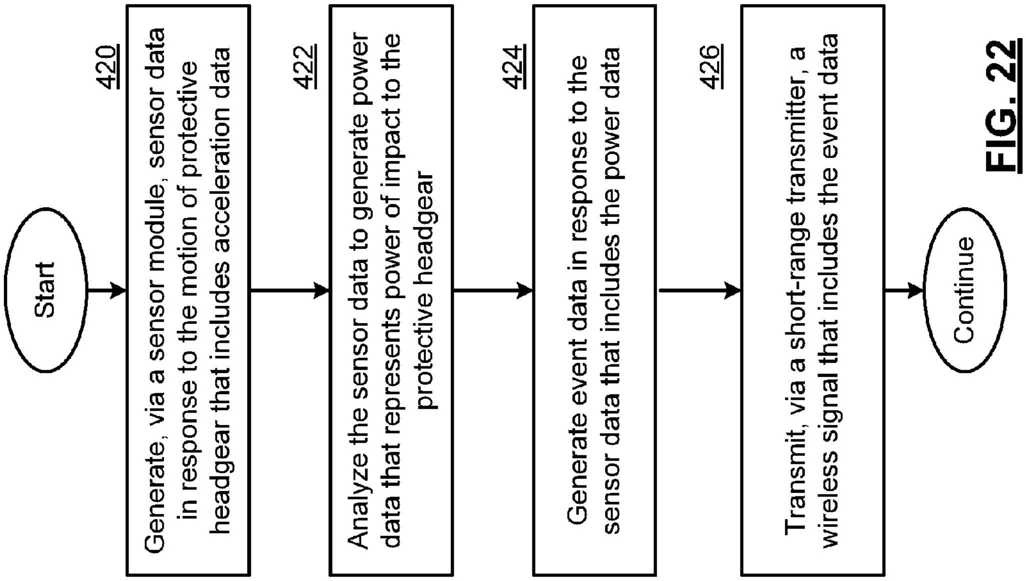
FIG. 22 presents a flowchart representation of a method in accordance with an embodiment of the present invention.

FIG. 22 presents a flowchart representation of a method in accordance with an embodiment of the present invention. In particular, a method is shown for use in conjunction with one or more functions and features described in conjunction with FIGS. 1-21. In step 420, sensor data that includes acceleration data is generated via a sensor module, in response to an impact to the protective headgear. In step 422, sensor data is analyzed to generate power data that represents power of impact to the protective headgear. In step 424, event data is generated that includes the power data. In step 426, a wireless signal that includes the event data is transmitted, via a short-range wireless transmitter.

In an embodiment of the present invention, the wireless signal is transmitted to an adjunct device that is coupled to a handheld communication device for processing of the event data by the handheld communication device. Step 422 can include generating velocity data and the event data is generated in step 424 to further include the velocity data. Step 422 can include generating displacement data and the event data is generated in step 424 to further include the displacement data.

Figure 23:
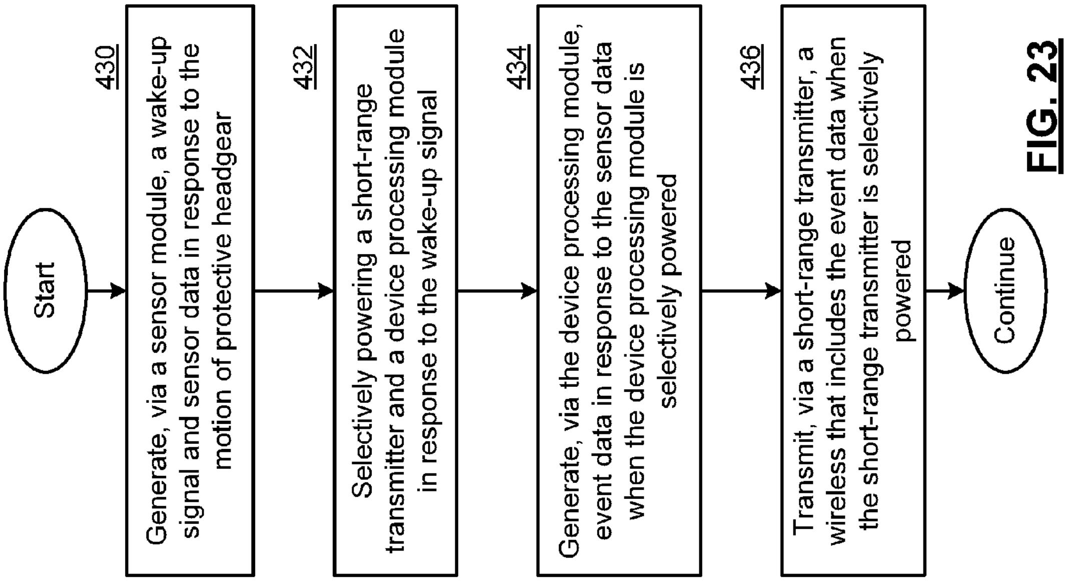
FIG. 23 presents a flowchart representation of a method in accordance with an embodiment of the present invention.

FIG. 23 presents a flowchart representation of a method in accordance with an embodiment of the present invention. In particular, a method is shown for use in conjunction with one or more functions and features described in conjunction with FIGS. 1-22. In step 430, a wake-up signal and sensor data that includes acceleration data are generated, via a sensor module, in response to an impact to the protective headgear. In step 432, a short-range transmitter and a device processing module are selectively powered in response to the wake-up signal. In step 434, event data is generated in response to the sensor data via the device processing module, when the device processing module is selectively powered. In step 436, a wireless signal that includes the event data is transmitted, via the short-range wireless transmitter, when the short-range transmitter is selectively powered.

In an embodiment of the present invention, the wireless signal is transmitted to an adjunct device that is coupled to a handheld communication device for processing of the event data by the handheld communication device. The first sensor data can be generated in response to the wake-up signal. The first wake-up signal can be generated when an acceleration signal compares favorably to a first signal threshold or by a kinetic sensor, etc.

Figure 24:
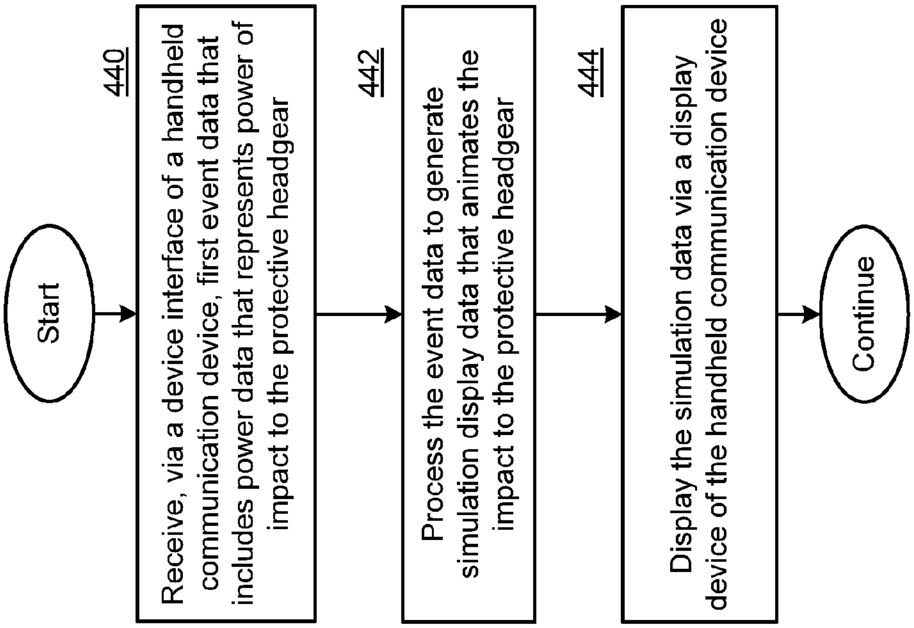
FIG. 24 presents a flowchart representation of a method in accordance with an embodiment of the present invention.

FIG. 24 presents a flowchart representation of a method in accordance with an embodiment of the present invention. In particular, a method is shown for use in conjunction with one or more functions and features described in conjunction with FIGS. 1-23. In step 440, first event data that includes power data that represents power of impact to the protective headgear is received, via a device interface of the handheld communication device. In step 442, the event data is processed to generate simulation display data that animates the impact to the protective headgear. In step 444, the simulation display data is displayed via a display device of the handheld communication device.

In an embodiment of the present invention, the device interface includes a communication port that receives the event data from a first wireless device coupled to the protective headgear via an adjunct device connected to the communication port. The device interface can includes an RF transceiver that receives the event data from a first wireless device coupled to the protective headgear. The event data can be received from a plurality of wireless devices coupled to the protective headgear. The event data can further include velocity data that represents velocity of impact to the protective headgear and/or displacement data that represents displacement of impact to the protective headgear.

Step 442 can include modeling at least one of: shock absorbing capabilities of the protective headgear, a human head that simulates a head of a wearer of the protective headgear, and a human brain that simulates a brain of the wearer of the protective headgear. The simulation display data can animate the impact to the protective headgear by animating at least one of: the protective headgear, the human head, the human skull and the human brain.

The method can further include generating an alarm event signal in response to the event data and presenting, via the user interface, at least one of: an audible alarm or a visual alarm in response to the alarm event signal. In addition, the method can include transmitting, via a wireless telephony transceiver of the handheld communication device and in response to the alarm event signal, at least one of: the event data, and the simulation display data.

While the description above has set forth several different modes of operation, the devices described here may simultaneously be in two or more of these modes, unless, by their nature, these modes necessarily cannot be implemented simultaneously. While the foregoing description includes the description of many different embodiments and implementations, the functions and features of these implementations and embodiments can be combined in additional embodiments of the present invention not expressly disclosed by any single implementation or embodiment, yet nevertheless understood by one skilled in the art when presented this disclosure.

As one of ordinary skill in the art will appreciate, the term “substantially” or “approximately”, as may be used herein, provides an industry-accepted tolerance to its corresponding term and/or relativity between items. Such an industry-accepted tolerance ranges from less than one percent to twenty percent and corresponds to, but is not limited to, component values, integrated circuit process variations, temperature variations, rise and fall times, and/or thermal noise. Such relativity between items ranges from a difference of a few percent to magnitude differences. As one of ordinary skill in the art will further appreciate, the term “coupled”, as may be used herein, includes direct coupling and indirect coupling via another component, element, circuit, or module where, for indirect coupling, the intervening component, element, circuit, or module does not modify the information of a signal but may adjust its current level, voltage level, and/or power level. As one of ordinary skill in the art will also appreciate, inferred coupling (i.e., where one element is coupled to another element by inference) includes direct and indirect coupling between two elements in the same manner as “coupled”. As one of ordinary skill in the art will further appreciate, the term “compares favorably”, as may be used herein, indicates that a comparison between two or more elements, items, signals, etc., provides a desired relationship. For example, when the desired relationship is that signal 1 has a greater magnitude than signal 2, a favorable comparison may be achieved when the magnitude of signal 1 is greater than that of signal 2 or when the magnitude of signal 2 is less than that of signal 1.

In preferred embodiments, the various circuit components are implemented using 0.35 micron or smaller CMOS technology and can include one or more system on a chip integrated circuits that implement any combination of the devices, modules, submodules and other functional components presented herein. Provided however that other circuit technologies including other transistor, diode and resistive logic, both integrated or non-integrated, may be used within the broad scope of the present invention. Likewise, various embodiments described herein can also be implemented as software programs running on a computer processor. It should also be noted that the software implementations of the present invention can be stored on a tangible storage medium such as a magnetic or optical disk, read-only memory or random access memory and also be produced as an article of manufacture.

Thus, there has been described herein an apparatus and method, as well as several embodiments including a preferred embodiment. Various embodiments of the present invention herein-described have features that distinguish the present invention from the prior art.

It will be apparent to those skilled in the art that the disclosed invention may be modified in numerous ways and may assume many embodiments other than the preferred forms specifically set out and described above. Accordingly, it is intended by the appended claims to cover all modifications of the invention which fall within the true spirit and scope of the invention.

What is claimed is:

1. A system for monitoring protective headgear, the system comprising:

a first wireless device that includes:

a first sensor module, coupled to the protective headgear that generates first sensor data in response to an impact to the protective headgear;

a first device processing module, coupled to the first sensor module, that generates first event data in response to the first sensor data, wherein the first device processing module determines a quiescent period during a period of normal operation, generates a gravitational correction during the quiescent period and generates the first event data based on the gravitational correction; and a first short-range wireless transmitter, coupled to the first sensor module and the first device processing module, that transmits a first wireless signal that includes the first event data; and an adjunct device that includes:

an adjunct housing that is coupleable to a handheld communication device via a communication port of the handheld communication device;

an adjunct short-range wireless receiver, coupled to the adjunct housing, that receives the first wireless signal and recovers the first event data; and an adjunct processing module that transfers the first event data to the handheld communication device via the communication port of the handheld communication device.

2. The system of claim 1 wherein the first sensor module includes an accelerometer and a gyroscope and wherein the first sensor data includes linear acceleration data and rotational velocity data.

3. The system of claim 2 wherein the accelerometer responds to acceleration of the protective headgear along a plurality of axes and wherein the linear acceleration data indicates the acceleration of the protective headgear along the plurality of axes.

4. The system of claim 2 wherein the gyroscope responds to velocity of the protective headgear along a plurality of axes and wherein the rotational velocity data indicates the velocity of the protective headgear along the plurality of axes.

5. The system of claim 1 further comprising:

a second wireless device that includes:

a second sensor module, coupled to the protective headgear that generates second sensor data in response to an impact to the protective headgear;

a second device processing module, coupled to the second sensor module, that generates second event data in response to the second sensor data; and a second short-range wireless transmitter, coupled to the second sensor module and the second device processing module, that transmits a second wireless signal that includes the second event data; and wherein the adjunct short-range wireless receiver receives the second wireless signal and recovers the second event data; and wherein the adjunct processing module transfers the second event data to the handheld communication device via the communication port of the handheld communication device.

6. The system of claim 1 wherein the protective headgear includes a football helmet.

7. The system of claim 1 wherein the protective headgear includes a first helmet and a second helmet, wherein the first sensor module is coupled to the first helmet and generates the first sensor data in response to motion of the first helmet, and wherein the system further comprises:

a second wireless device that includes:

a second sensor module, coupled to the second helmet that generates second sensor data in response to motion of the second helmet;

a second device processing module, coupled to the second sensor module, that generates second event data in response to the second sensor data; and a second short-range wireless transmitter, coupled to the second sensor module and the second device processing module, that transmits a second wireless signal that includes the second event data; and wherein the adjunct short-range wireless receiver receives the second wireless signal and recovers the second event data; and wherein the adjunct processing module transfers the second event data to the handheld communication device via the communication port of the handheld communication device.

8. A wireless device for use in a system for monitoring protective headgear, the wireless device comprising:

a sensor module, coupled to the protective headgear that generates sensor data in response to an impact to the protective headgear, wherein the sensor module includes an accelerometer and a gyroscope and wherein the sensor data includes linear acceleration data and rotational velocity data;

a device processing module, coupled to the sensor module, that generates event data in response to the sensor data, wherein the device processing module determines a quiescent period during a period of normal operation, generates a gravitational correction during the quiescent period and generates the event data based on the gravitational correction; and a short-range wireless transmitter, coupled to the sensor module and the device processing module, that transmits a wireless signal that includes the event data.

9. The wireless device of claim 8 wherein the short-range wireless transmitter transmits the wireless signal to an adjunct device that is coupled to a handheld communication device for processing of the event data by the handheld communication device.

10. The wireless device of claim 8 wherein the accelerometer responds to acceleration of the protective headgear along a plurality of axes and wherein the linear acceleration data indicates the acceleration of the protective headgear along the plurality of axes.

11. The wireless device of claim 8 wherein the gyroscope responds to velocity of the protective headgear along a plurality of axes and wherein the rotational velocity data indicates the velocity of the protective headgear along the plurality of axes.

12. The wireless device of claim 8 wherein the protective headgear includes a football helmet.

13. A method for use in a system for monitoring protective headgear, the method comprising:

generating, via a sensor module, sensor data in response to an impact to the protective headgear, wherein the sensor module includes an accelerometer and a gyroscope and wherein the sensor data includes linear acceleration data and rotational velocity data;

generating event data in response to the sensor data, wherein generating the event data includes:

determining a quiescent period during a period of normal operation;

generating a gravitational correction during the quiescent period; and generates the event data based on the gravitational correction; and transmitting, via a short-range wireless transmitter, a wireless signal that includes the event data.

14. The method of claim 13 wherein the wireless signal is transmitted to an adjunct device that is coupled to a handheld communication device for processing of the event data by the handheld communication device.

15. The method of claim 13 wherein the accelerometer responds to acceleration of the protective headgear along a plurality of axes and wherein the linear acceleration data indicates the acceleration of the protective headgear along the plurality of axes.

16. The method of claim 13 wherein the gyroscope responds to velocity of the protective headgear along a plurality of axes and wherein the rotational velocity data indicates the velocity of the protective headgear along the plurality of axes.

17. The method of claim 13 wherein the protective headgear includes a football helmet.

* * * * *